US011723678B2

(12) United States Patent
Follmer et al.

(10) Patent No.: US 11,723,678 B2
(45) Date of Patent: *Aug. 15, 2023

(54) APPARATUS, SYSTEM, AND METHOD FOR VASCULATURE OBSTRUCTION REMOVAL

(71) Applicant: Progressive NEURO, Inc., Ravenna, NE (US)

(72) Inventors: Brett Allen Follmer, Santa Clara, CA (US); Arturo S. Rosqueta, San Jose, CA (US); Tiffany Tran Ngo, San Jose, CA (US); Kirk Zeller, Ravenna, NE (US)

(73) Assignee: Progressive NEURO, Inc., Ravenna, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/547,970

(22) Filed: Dec. 10, 2021

(65) Prior Publication Data
US 2022/0096107 A1   Mar. 31, 2022

Related U.S. Application Data

(63) Continuation of application No. 17/317,244, filed on May 11, 2021, now Pat. No. 11,197,685, which is a
(Continued)

(51) Int. Cl.
*A61B 17/221* (2006.01)
*A61B 17/22* (2006.01)

(52) U.S. Cl.
CPC .... *A61B 17/221* (2013.01); *A61B 2017/2215* (2013.01); *A61B 2017/22079* (2013.01)

(58) Field of Classification Search
CPC ........ A61B 17/221; A61B 2017/22079; A61B 2017/2215; A61B 17/225; A61B 17/2251;
(Continued)

(56) References Cited

U.S. PATENT DOCUMENTS

| 4,886,061 A | 12/1989 | Fischell et al. |
| 4,926,858 A | 5/1990 | Gifford, III et al. |

(Continued)

FOREIGN PATENT DOCUMENTS

| CN | 109199533 A | 1/2019 |
| DE | 19811364 A1 | 9/1999 |

(Continued)

OTHER PUBLICATIONS

International Search Report dated Jan. 30, 2020 for PCT/US2019/061137.
(Continued)

*Primary Examiner* — Kankindi Rwego
(74) *Attorney, Agent, or Firm* — Nasr Patent Law LLC; Faisal K. Abou-Nasr

(57) ABSTRACT

An obstruction removal device is configured to be inserted through a catheter and at least partially extended into a vasculature from a distal end of the catheter. The obstruction removal device includes: a base member configured to engage one or more guide stops at the distal end of the catheter; a tubular member coupled to the base member and configured to apply a suction force from the catheter to an obstruction to remove the obstruction from the vasculature; and an expandable member surrounding the tubular member. The expandable member is configured to transition from a contracted state to an expanded state after the expandable member is at least partially extended into the vasculature from the distal end of the catheter. The expandable member is further configured to at least partially surround the obstruction as the obstruction is being removed from the vasculature.

11 Claims, 29 Drawing Sheets

Related U.S. Application Data continuation-in-part of application No. 16/572,150, filed on Sep. 16, 2019, now Pat. No. 11,253,279.

(60) Provisional application No. 63/140,433, filed on Jan. 22, 2021, provisional application No. 62/767,852, filed on Nov. 15, 2018.

(58) Field of Classification Search
CPC .. A61B 2017/00287; A61B 2017/2212; A61B 2017/2217; A61B 2017/2253; A61B 2017/2256; A61B 2017/2258; A61B 2017/32007; A61B 2217/005; A61M 3/0279; A61M 25/0119
USPC ........................................................ 606/127
See application file for complete search history.

(56) References Cited

U.S. PATENT DOCUMENTS

| | | |
|---|---|---|
| 4,997,435 A | 3/1991 | Demeter |
| 5,772,674 A | 6/1998 | Nakhjavan |
| 6,210,370 B1 | 4/2001 | Chi-Sing et al. |
| 6,309,399 B1 | 10/2001 | Barbut et al. |
| 6,419,291 B1 | 7/2002 | Preta |
| 6,800,085 B2 | 10/2004 | Selmon et al. |
| 7,041,117 B2 | 5/2006 | Suon et al. |
| 8,608,754 B2 | 12/2013 | Wensel et al. |
| 8,777,976 B2 | 7/2014 | Brady et al. |
| 8,801,748 B2 | 8/2014 | Martin |
| 8,986,241 B2 | 3/2015 | Evans et al. |
| 9,125,728 B2 | 9/2015 | Angel et al. |
| 9,149,609 B2 | 10/2015 | Ansel et al. |
| 9,463,035 B1 | 10/2016 | Greenhalgh et al. |
| 9,597,171 B2 | 3/2017 | Shrivastava et al. |
| 9,833,252 B2 | 12/2017 | Sepetka et al. |
| 9,943,323 B2 | 4/2018 | Martin et al. |
| 9,987,028 B2 | 6/2018 | Lowinger et al. |
| 10,070,878 B2 | 9/2018 | Ma |
| 10,076,347 B2 | 9/2018 | Sepetka et al. |
| 10,143,482 B2 | 12/2018 | Nguyen et al. |
| 10,172,633 B2 | 1/2019 | Martin et al. |
| 10,231,751 B2 | 3/2019 | Sos |
| 10,271,863 B2 | 4/2019 | Marks et al. |
| 10,314,600 B2 | 6/2019 | Morsi |
| 10,383,644 B2 | 8/2019 | Molaei et al. |
| 11,197,685 B2 * | 12/2021 | Follmer .................. A61B 17/22 |
| 2007/0191866 A1 | 8/2007 | Palmer et al. |
| 2008/0082107 A1 * | 4/2008 | Miller .................. A61B 17/221 |
| | | 606/127 |
| 2009/0198269 A1 | 8/2009 | Hannes et al. |
| 2009/0222035 A1 | 9/2009 | Schneiderman |
| 2010/0131000 A1 | 5/2010 | DeMello et al. |
| 2010/0249815 A1 | 9/2010 | Jantzen et al. |
| 2011/0060359 A1 | 3/2011 | Hannes et al. |
| 2012/0041449 A1 | 2/2012 | Eckhouse et al. |
| 2013/0006284 A1 | 1/2013 | Aggerholm et al. |
| 2013/0325051 A1 | 12/2013 | Martn et al. |
| 2014/0074144 A1 | 3/2014 | Shrivastava et al. |
| 2014/0257245 A1 | 9/2014 | Rosenbluth et al. |
| 2015/0265299 A1 | 9/2015 | Cooper et al. |
| 2016/0135829 A1 | 5/2016 | Holochwost et al. |
| 2016/0361077 A1 | 12/2016 | Marks et al. |
| 2017/0325830 A1 | 11/2017 | Martin et al. |
| 2018/0008393 A1 | 1/2018 | Volobuyev et al. |
| 2018/0036028 A1 | 2/2018 | Krolik et al. |
| 2018/0070968 A1 * | 3/2018 | Wallace ........... A61B 17/22031 |
| 2018/0206865 A1 | 7/2018 | Martin et al. |
| 2018/0221037 A1 | 8/2018 | Martin et al. |
| 2018/0256177 A1 | 9/2018 | Cooper et al. |
| 2018/0325647 A1 | 11/2018 | Hauser |
| 2019/0000492 A1 | 1/2019 | Casey et al. |
| 2019/0014121 A1 | 1/2019 | Martin |
| 2019/0125396 A1 | 5/2019 | Avneri et al. |
| 2019/0239905 A1 | 8/2019 | Olson et al. |
| 2019/0298396 A1 | 10/2019 | Gamba et al. |
| 2019/0314606 A1 | 10/2019 | di Palma et al. |
| 2021/0267613 A1 | 9/2021 | Follmer et al. |

FOREIGN PATENT DOCUMENTS

| | | |
|---|---|---|
| EP | 1237489 A1 | 9/2002 |
| EP | 2470088 B1 | 6/2017 |
| EP | 3505091 A1 | 7/2019 |
| JP | 2018134534 A | 8/2018 |
| WO | 2019195336 A1 | 10/2010 |
| WO | 2014002087 A1 | 1/2014 |
| WO | 2018043279 A1 | 3/2018 |
| WO | 2018043281 A1 | 3/2018 |
| WO | 2018118706 A1 | 6/2018 |
| WO | 2018160935 A1 | 9/2018 |
| WO | 2019051425 A1 | 3/2019 |

OTHER PUBLICATIONS

International Search Report dated Apr. 11, 2022 for PCT/US2022/013306.

* cited by examiner

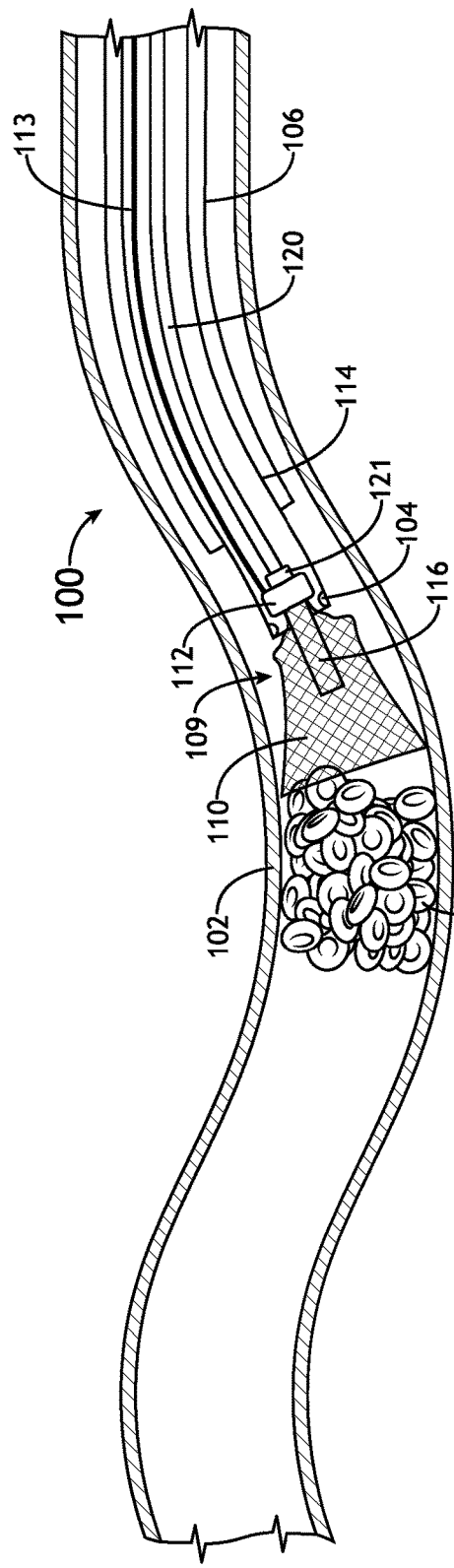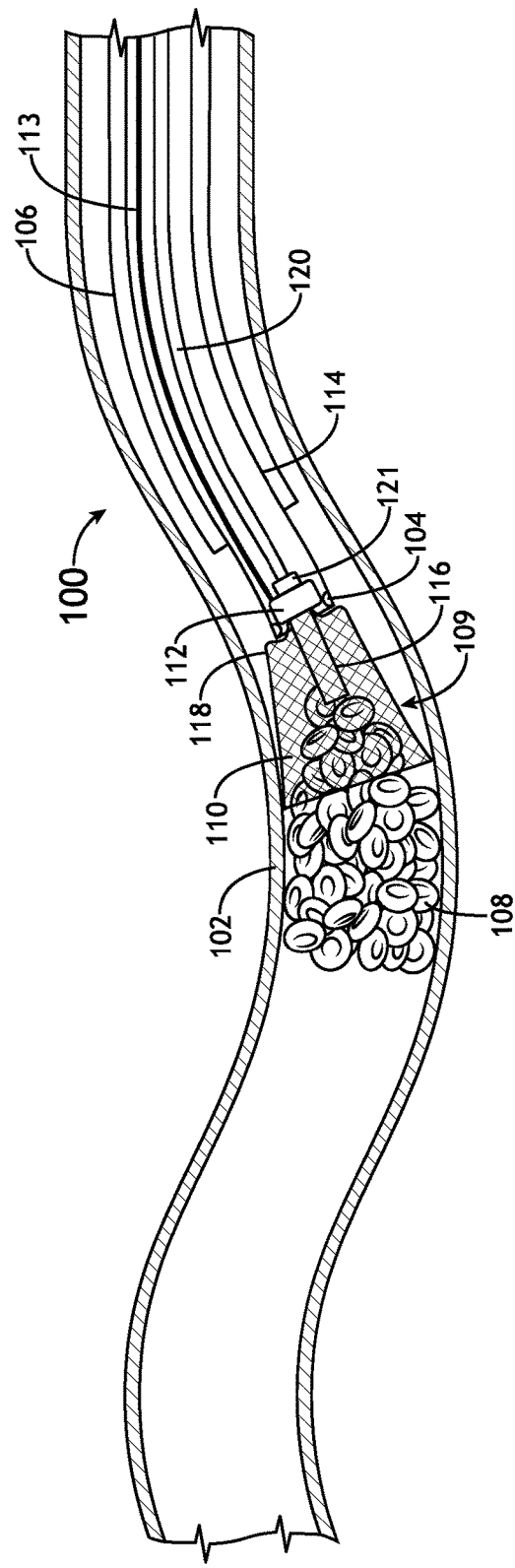

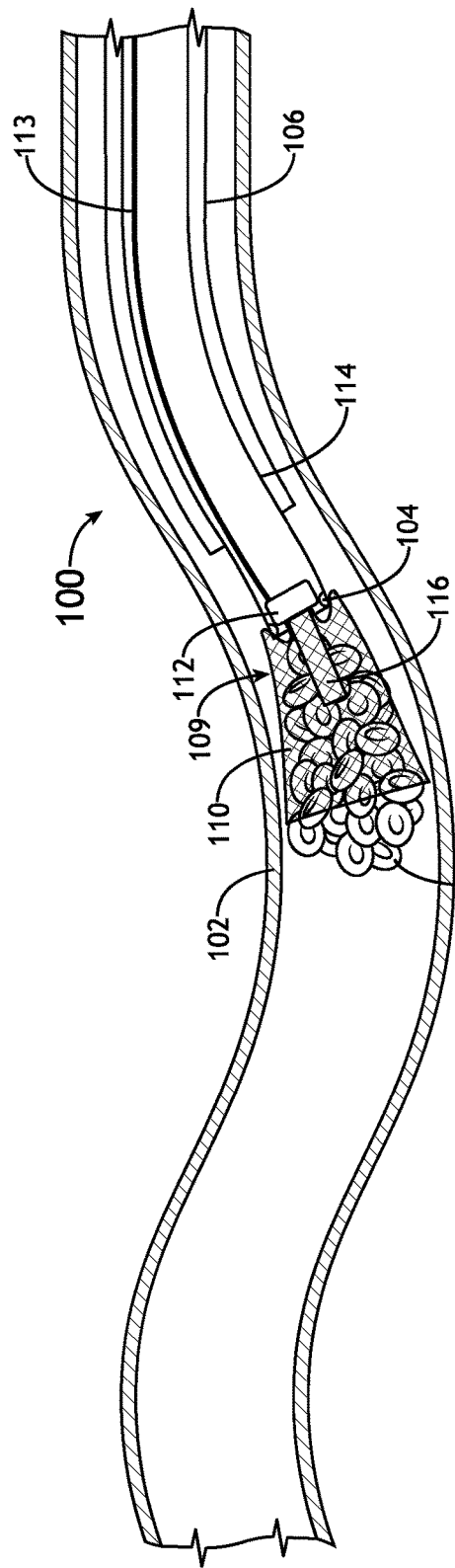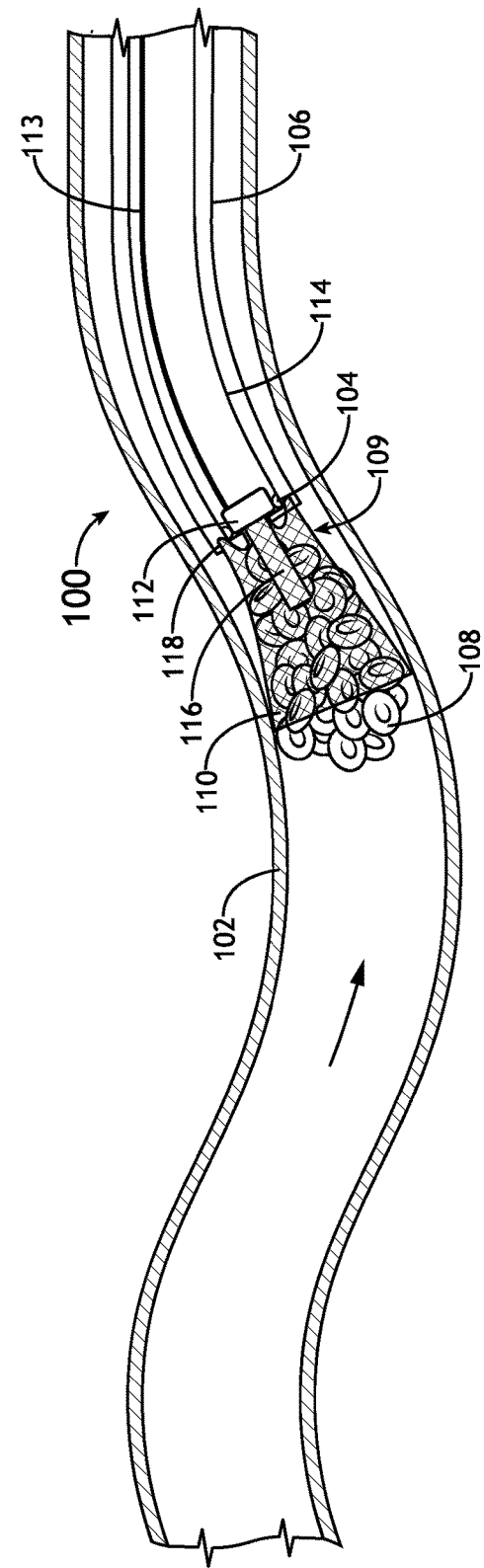
FIG.1G
FIG.1H

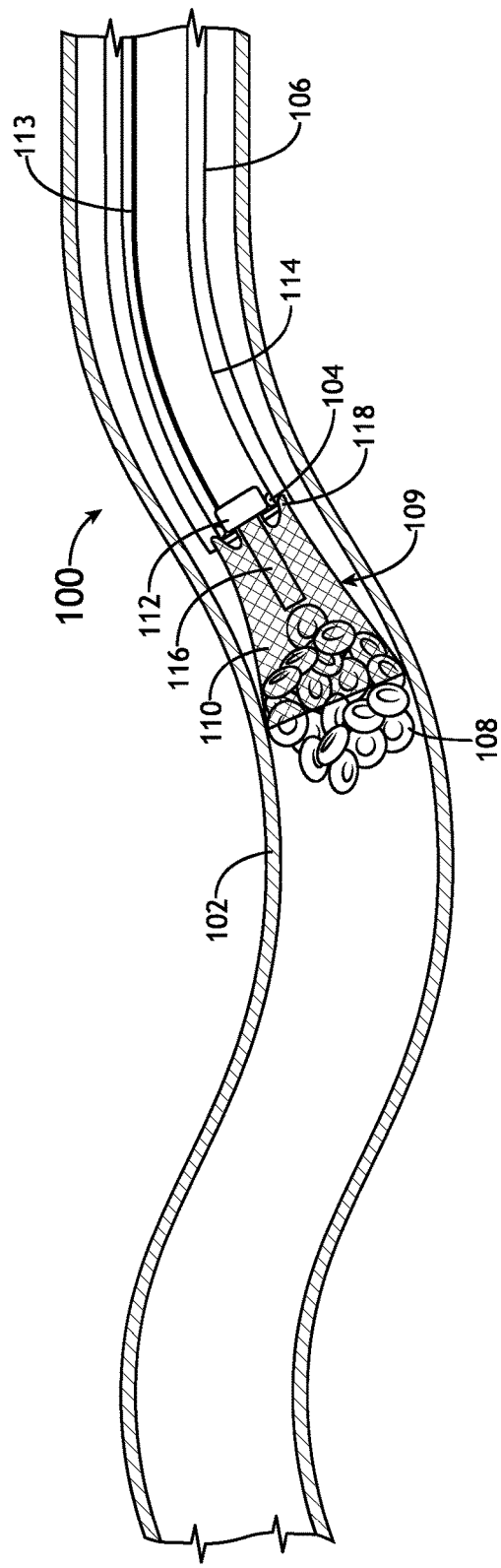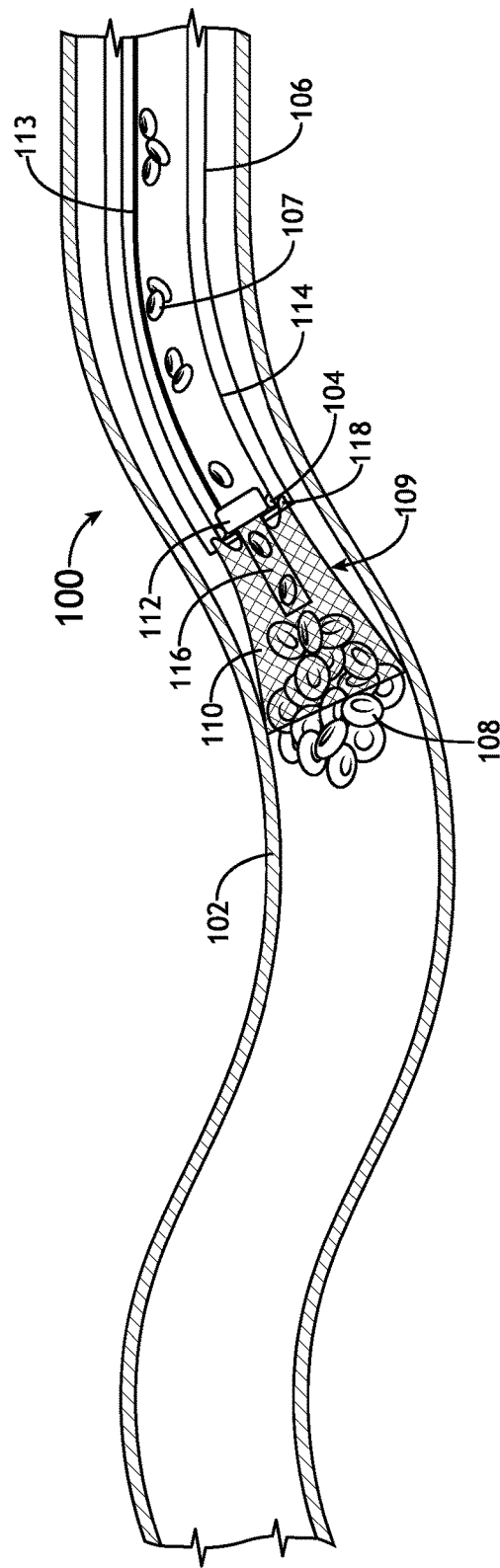

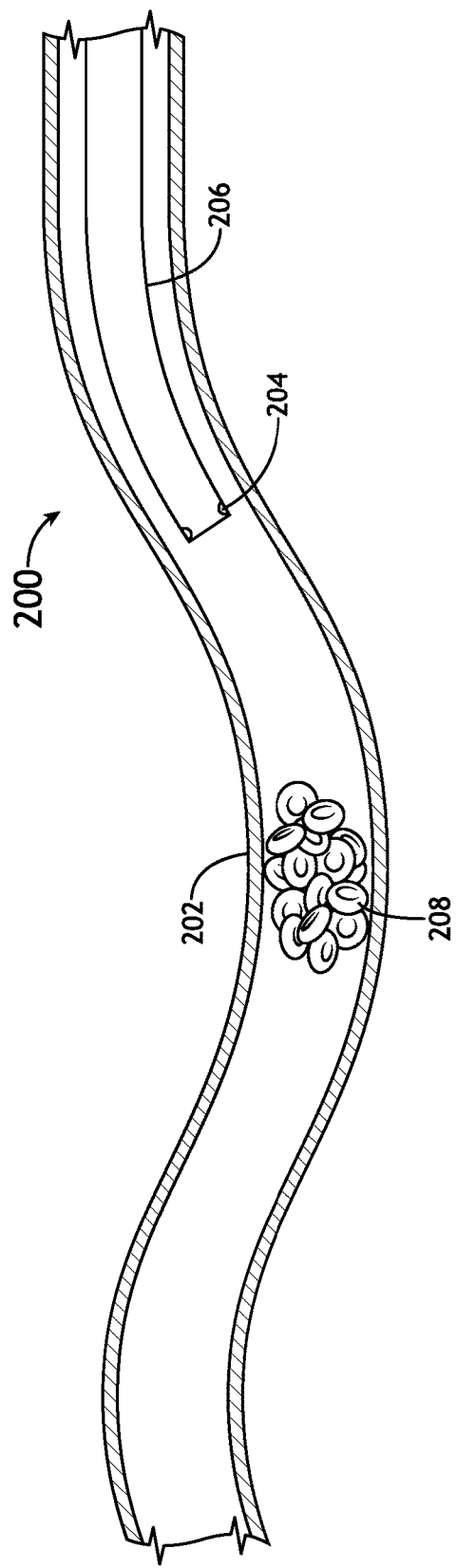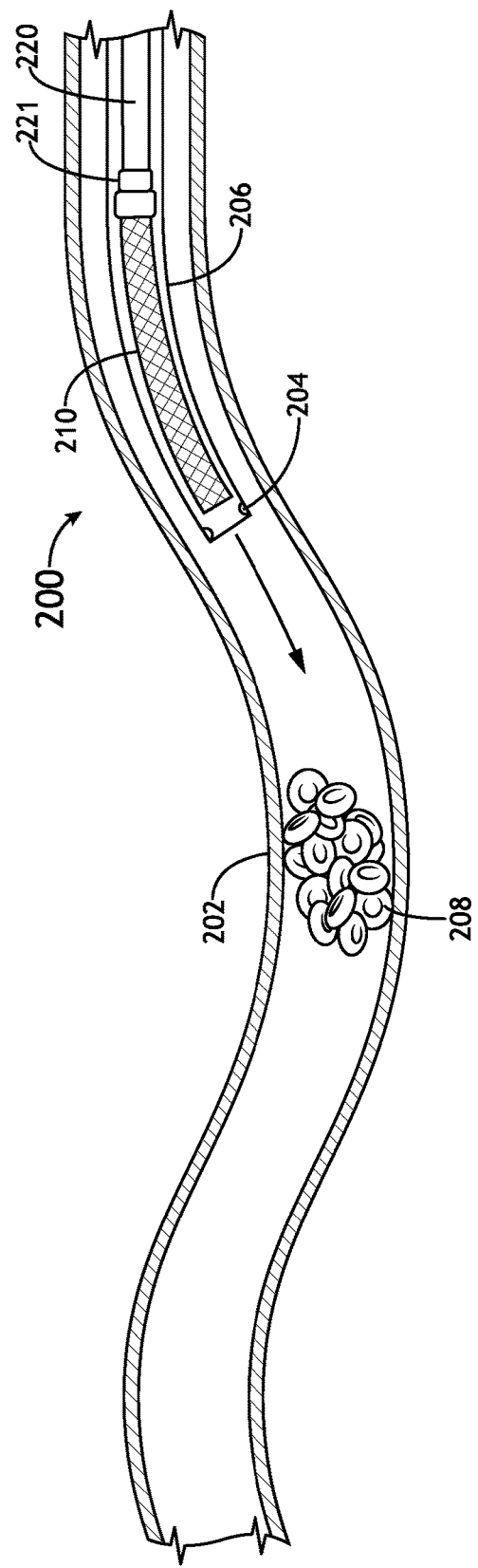

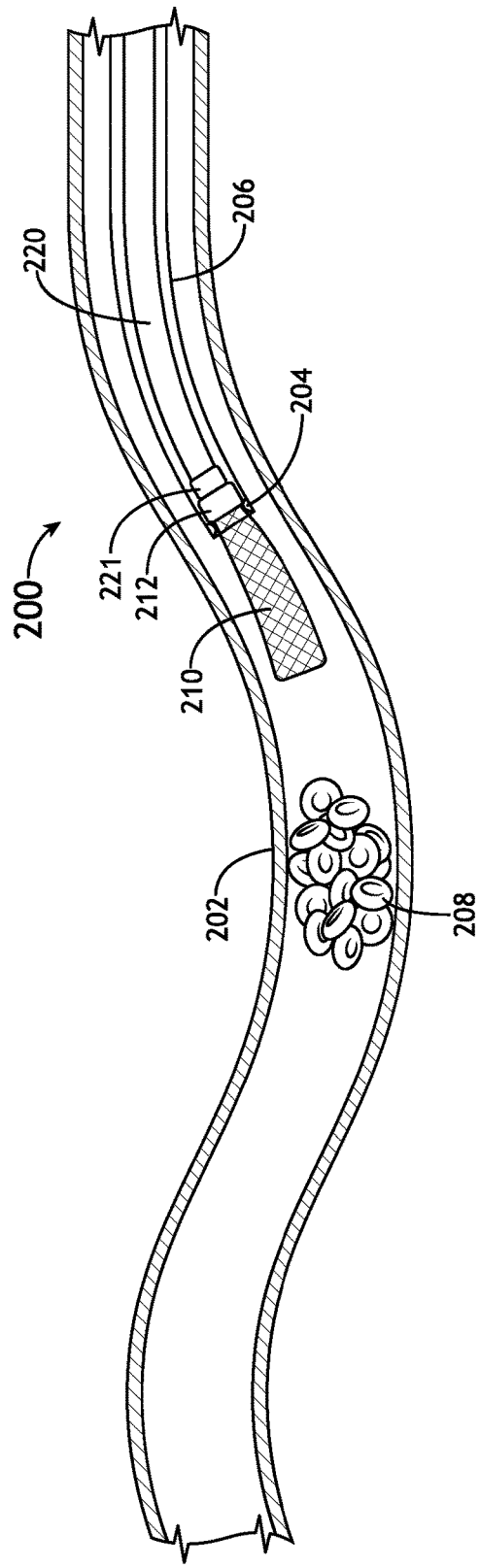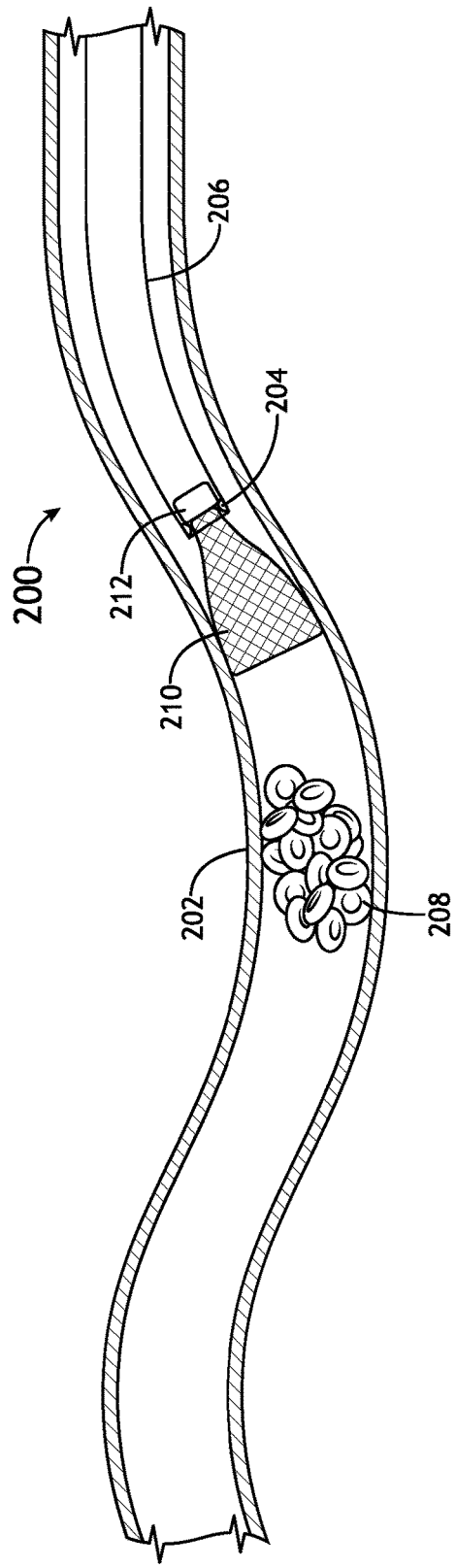
FIG.2C
FIG.2D

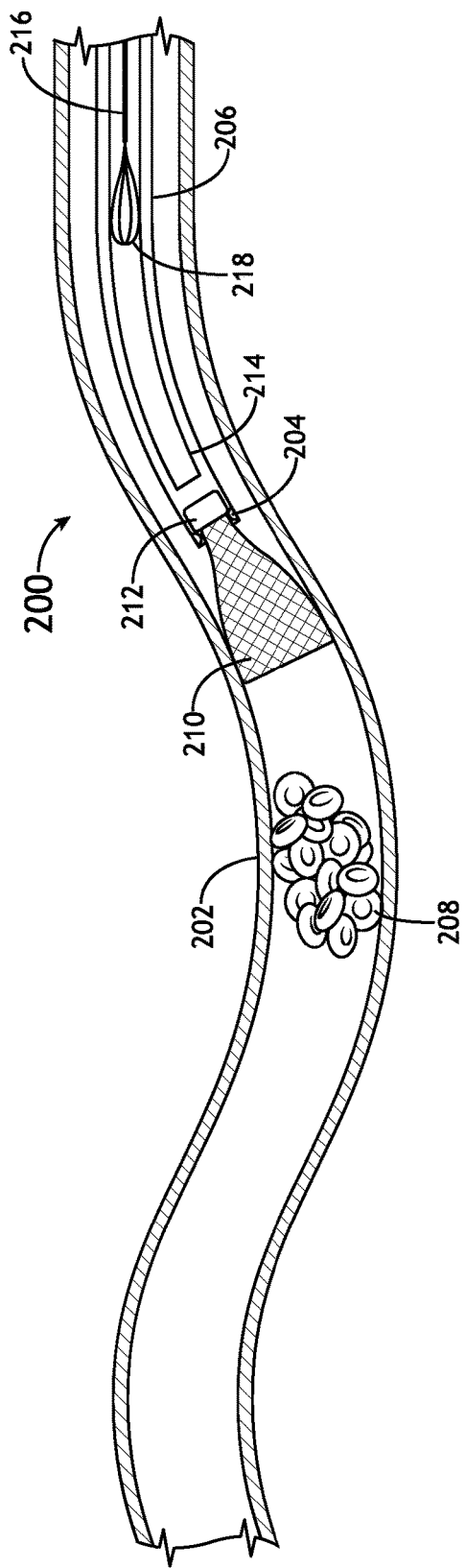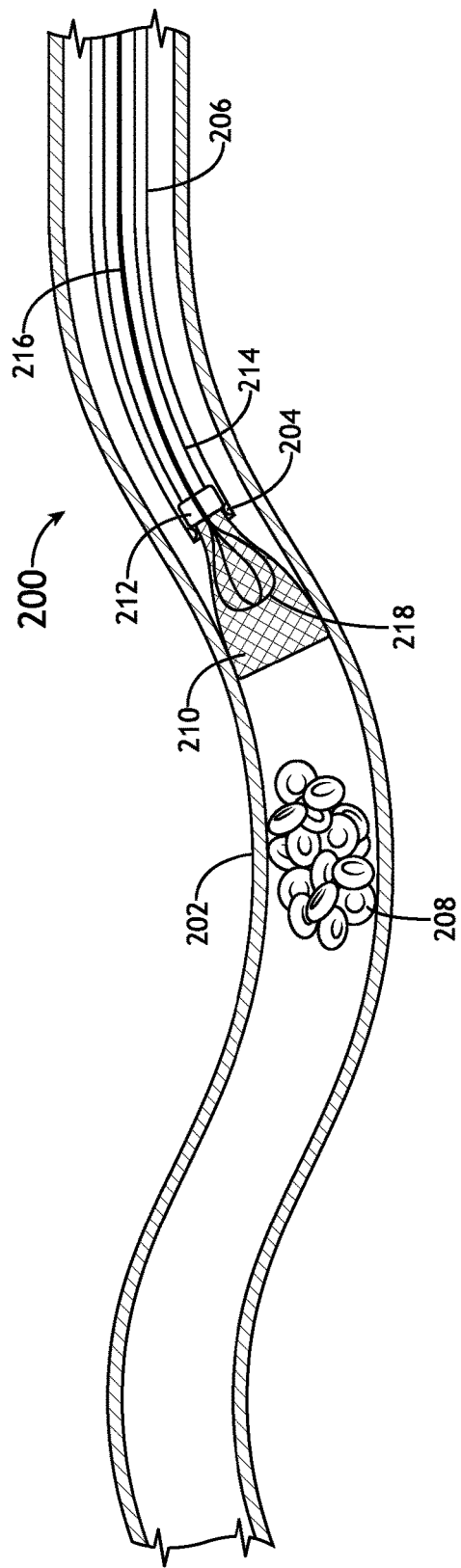

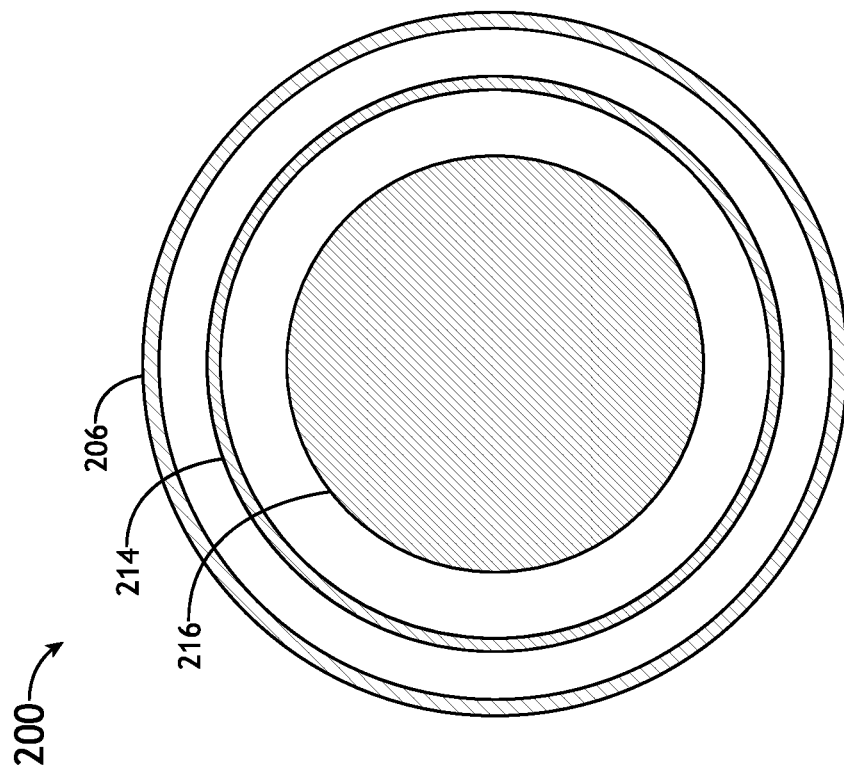

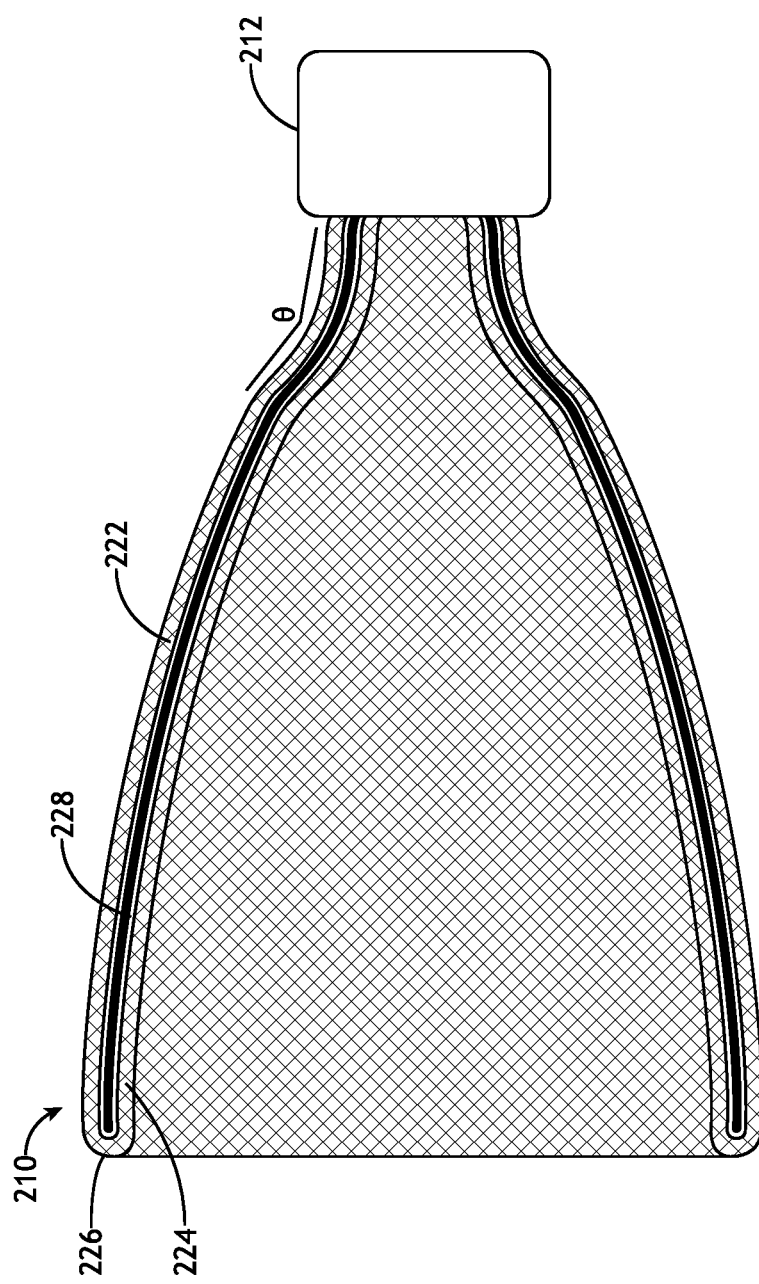

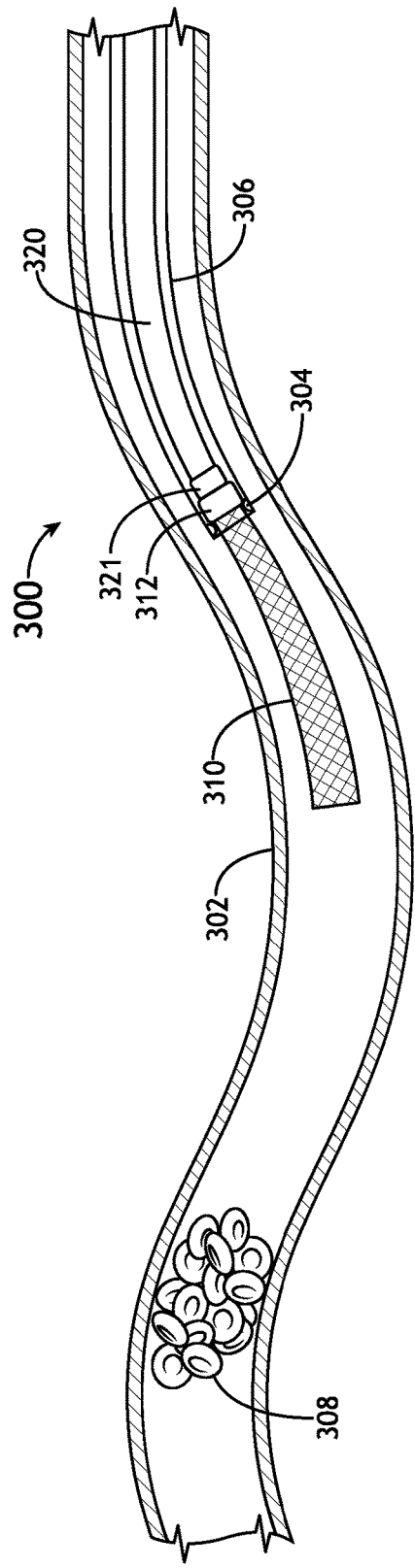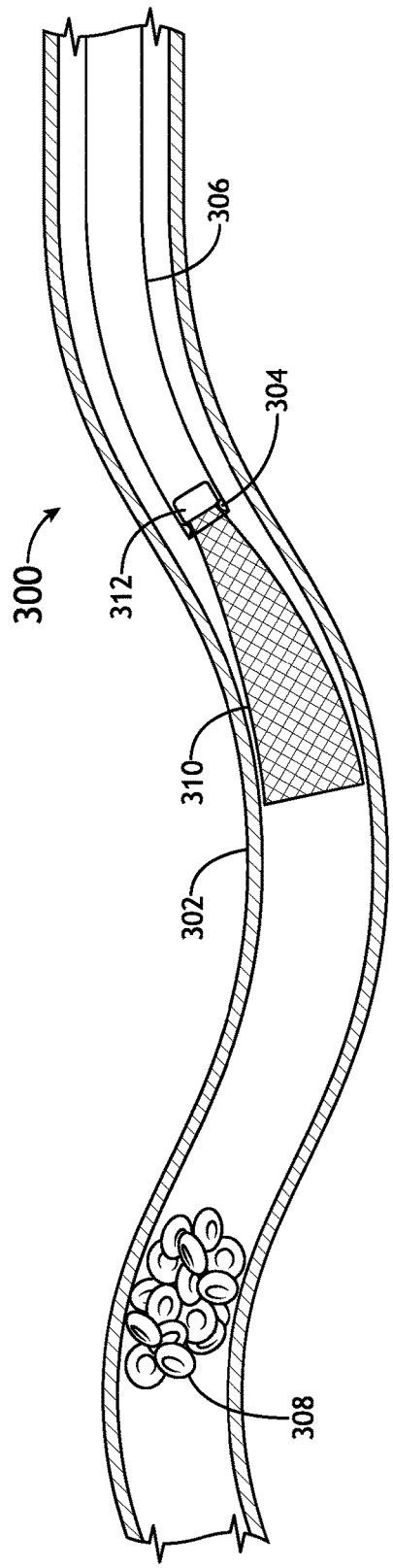
FIG.3C
FIG.3D

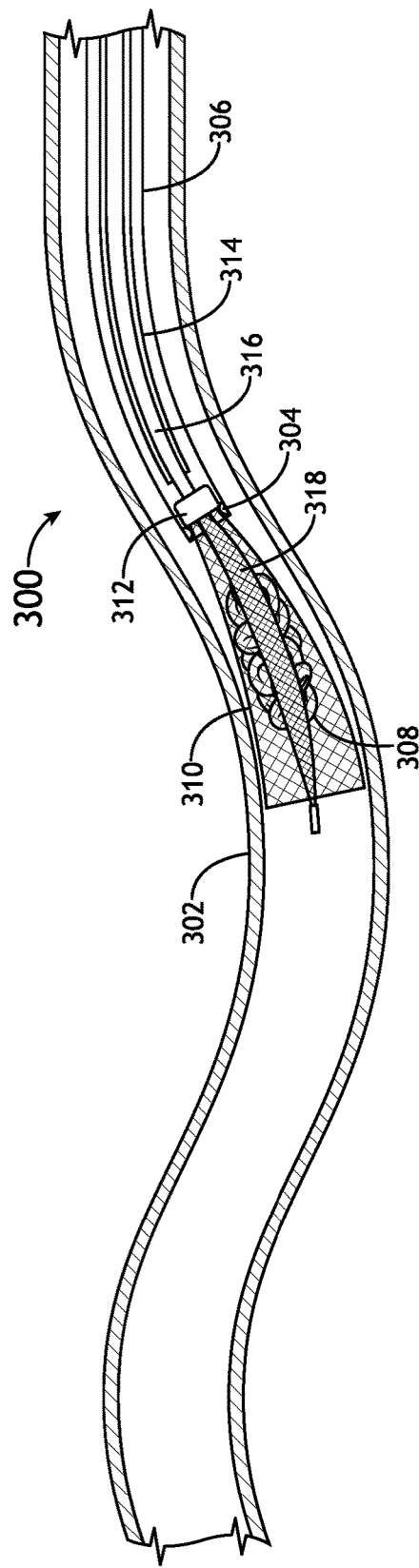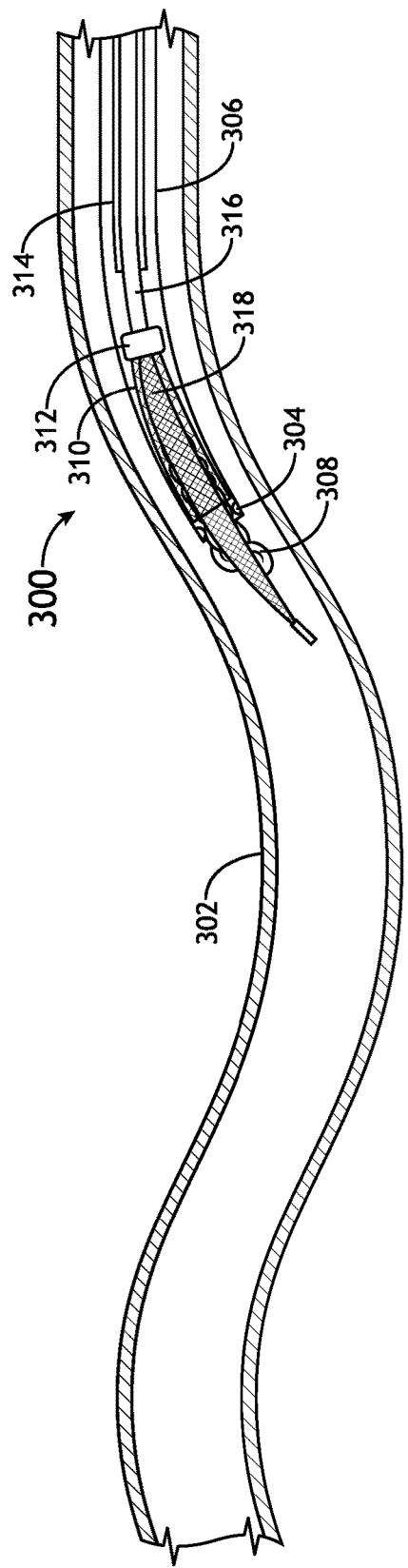

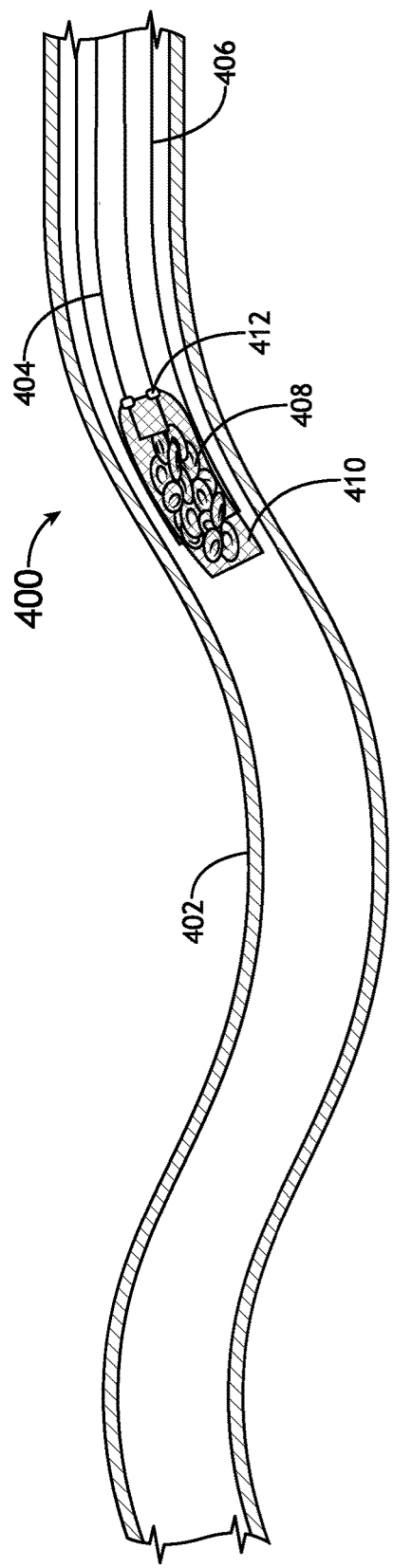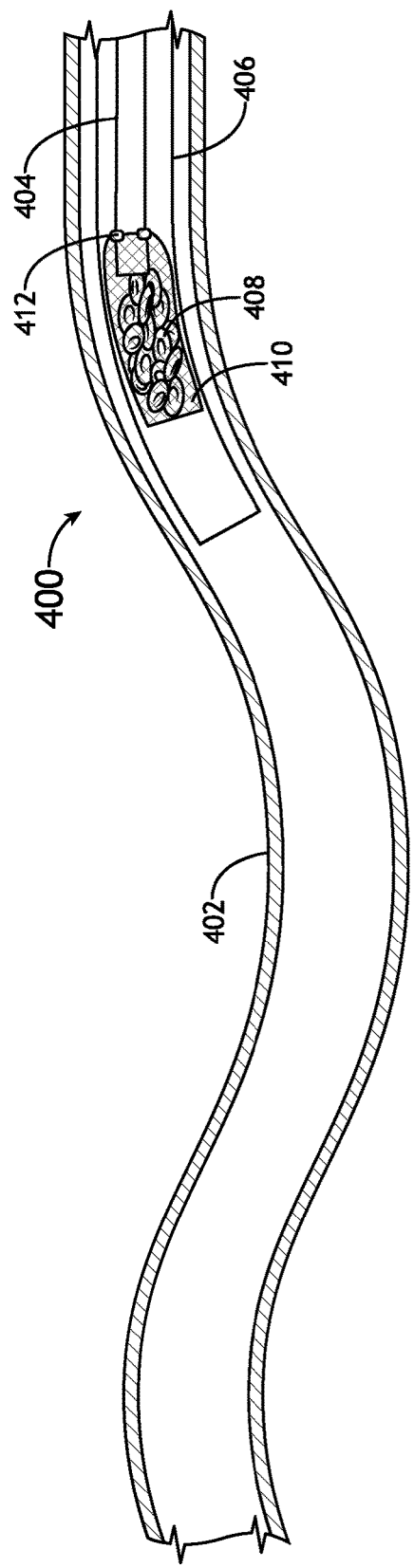

APPARATUS, SYSTEM, AND METHOD FOR VASCULATURE OBSTRUCTION REMOVAL

CROSS-REFERENCE TO RELATED APPLICATIONS

The present application is a continuation of U.S. Nonprovisional application Ser. No. 17/317,244, filed May 11, 2021, and titled "APPARATUS, SYSTEM, AND METHOD FOR VASCULATURE OBSTRUCTION REMOVAL," which claims the benefit under 35 U.S.C. § 119(e) of U.S. Provisional Application No. 63/140,433, filed Jan. 22, 2021, and titled "APPARATUS, SYSTEM, AND METHOD FOR VASCULATURE OBSTRUCTION REMOVAL." U.S. Nonprovisional application Ser. No. 17/317,244 is also a continuation-in-part of U.S. Nonprovisional application Ser. No. 16/572,150, filed Sep. 16, 2019, and titled "APPARATUS, SYSTEM, AND METHOD FOR VASCULATURE OBSTRUCTION REMOVAL," which claims the benefit of U.S. Provisional Application No. 62/767,852, filed Nov. 15, 2018, and titled "APPARATUS, SYSTEM, AND METHOD FOR VASCULATURE OBSTRUCTION REMOVAL." Each of the related applications is incorporated herein by reference in its entirety.

TECHNICAL FIELD

The present invention generally relates to medical devices, and, more particularly, to medical devices for removing vascular obstructions.

BACKGROUND

Obstruction removal systems/devices may operate by lodging the obstruction in a component of the removal system. In some cases, the obstruction may dislodge. Dislodgement of the obstruction substantially increases the risk for potential complications, such as stroke or heart attack. Thus, it is desirable to secure the obstruction safely for removal from the body.

SUMMARY

An obstruction removal system, device and method are disclosed.

In one or more embodiments, an obstruction removal system includes a catheter and an obstruction removal device. The catheter is configured to be inserted within a vasculature. The catheter may have one or more guide stops located at a distal end of the catheter. The obstruction removal device is configured to be inserted through the catheter and at least partially extended into the vasculature from the distal end of the catheter.

In one or more embodiments, an obstruction removal device includes: a base member configured to engage one or more guide stops at the distal end of the catheter; a tubular member coupled to the base member and configured to apply a suction force from the catheter to an obstruction to remove the obstruction from the vasculature; and an expandable member surrounding the tubular member. The expandable member is configured to transition from a contracted state to an expanded state after the expandable member is at least partially extended into the vasculature from the distal end of the catheter. The expandable member is further configured to at least partially surround the obstruction as the obstruction is being removed from the vasculature.

In one or more embodiments, a method of removing an obstruction from a vasculature may include the steps of: (i) inserting a catheter into a vasculature, the catheter having one or more guide stops located at a distal end of the catheter; (ii) inserting an obstruction removal device through the catheter and at least partially extending the obstruction removal device into the vasculature from the distal end of the catheter, the obstruction removal device including a base member that engages the one or more guide stops at the distal end of the catheter, the obstruction removal device further including an expandable member and a tubular member; (iii) transitioning the expandable member from a contracted state to an expanded state after the expandable member is at least partially extended into the vasculature from the distal end of the catheter; and (iv) applying a suction force from the catheter to an obstruction, via the tubular member, to remove the obstruction from the vasculature, wherein the expandable member at least partially surrounds the obstruction as the obstruction is being removed from the vasculature.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

FIG. 1E illustrates a cross-sectional side view of the obstruction removal device being deployed through the catheter, wherein the obstruction removal device is pushed through the catheter by the delivery wire/tube until a base member of the obstruction removal device reaches one or more guide stops, and wherein an expandable member of the obstruction removal device transitions from a contracted state to an expanded state when the obstruction removal device is extended from a distal end of the catheter, in accordance with one or more embodiments of the present disclosure.

FIG. 1F illustrates a cross-sectional side view of the obstruction removal device being deployed through the catheter in proximity of an obstruction within the vasculature, in accordance with one or more embodiments of the present disclosure.

FIG. 1G illustrates a cross-sectional side view of the obstruction removal device after being deployed through the catheter in proximity of the obstruction within the vasculature, wherein the delivery wire/tube is removed and a suction force is applied from the catheter to suction an obstruction from the vasculature via a tubular member of the obstruction removal device, and wherein the expandable member surrounds the obstruction as the obstruction is being suctioned by the tubular member, in accordance with one or more embodiments of the present disclosure.

FIG. 1H illustrates a cross-sectional side view of the obstruction removal device and the catheter being drawn into a (larger) guide catheter to remove the obstruction from the vasculature while the expandable member surrounds the obstruction as the obstruction is being suctioned by the tubular member, in accordance with one or more embodiments of the present disclosure.

FIG. 1K illustrates a cross-sectional side view of the obstruction removal device after being deployed through the catheter in proximity of the obstruction within the vasculature, wherein the delivery wire/tube is removed and a suction force is applied from the catheter to suction an obstruction from the vasculature via a tubular member of the obstruction removal device, and wherein the expandable member surrounds the obstruction as the obstruction is being suctioned by the tubular member, in accordance with one or more embodiments of the present disclosure.

FIG. 1L illustrates a cross-sectional side view of the obstruction being suctioned from the vasculature via a tubular member of the obstruction removal device, wherein the obstruction is at least partially broken apart and suctioned into the catheter to remove the obstruction from the vasculature, in accordance with one or more embodiments of the present disclosure.

FIG. 1O illustrates a cross-sectional side view of the obstruction removal device of the obstruction removal system, in accordance with one or more embodiments of the present disclosure.

FIG. 2A illustrates a cross-sectional side view of a catheter of an obstruction removal system deployed within a vasculature, in accordance with one or more embodiments of the present disclosure.

FIG. 2B illustrates a cross-sectional side view of an expandable member of the obstruction removal system being deployed through the catheter, in accordance with one or more embodiments of the present disclosure.

FIG. 2C illustrates a cross-sectional side view of the expandable member of the obstruction removal system being deployed through the catheter until a base member of the expandable member reaches one or more guide stops, wherein the expandable member is pushed through the catheter by a delivery wire/tube, in accordance with one or more embodiments of the present disclosure.

FIG. 2D illustrates a cross-sectional side view of the expandable member of the obstruction removal system after being deployed through the catheter until a base member of the expandable member reaches one or more guide stops, wherein the delivery wire/tube is removed, and wherein the expandable member transitions from a contracted state to an expanded state when the expandable member is extended from a distal end of the catheter, in accordance with one or more embodiments of the present disclosure.

FIG. 2E illustrates a cross-sectional side view of an agitator of the obstruction removal system being deployed through the catheter, wherein the agitator is attached to a delivery tool that is fed through the catheter using a microcatheter, in accordance with one or more embodiments of the present disclosure.

FIG. 2F illustrates a cross-sectional side view of the agitator of the obstruction removal system being deployed through the catheter, wherein the agitator attached to the delivery tool is fed through the catheter and the expandable member using the microcatheter, in accordance with one or more embodiments of the present disclosure.

FIG. 2I illustrates a cross-sectional end view of a catheter with a microcatheter inserted within the catheter and a delivery tool inserted within the microcatheter, in accordance with one or more embodiments of the present disclosure.

FIG. 2M illustrates a cross-sectional side view of the expandable member of the obstruction removal system, in accordance with one or more embodiments of the present disclosure.

FIG. 3C illustrates a cross-sectional side view of the expandable member of the obstruction removal system being deployed through the catheter until a base member of the expandable member reaches one or more guide stops, wherein the expandable member is pushed through the catheter by a delivery wire/tube, in accordance with one or more embodiments of the present disclosure.

FIG. 3D illustrates a cross-sectional side view of the expandable member of the obstruction removal system being deployed through the catheter until a base member of the expandable member reaches one or more guide stops, wherein the delivery wire/tube is removed, and wherein the expandable member transitions from a collapsed state to an expanded state when the expandable member is extended from a distal end of the catheter, in accordance with one or more embodiments of the present disclosure.

FIG. 3I illustrates a cross-sectional side view of the stentriever of the obstruction removal system being drawn into the catheter to remove the obstruction from the vasculature, in accordance with one or more embodiments of the present disclosure.

FIG. 3J illustrates a cross-sectional side view of the expandable member of the obstruction removal system being pulled through the catheter with the stentriever, wherein the expandable member transitions to a contracted state and surrounds at least a portion of the obstruction as the expandable member is pulled into the catheter, in accordance with one or more embodiments of the present disclosure.

FIG. 4E illustrates a cross-sectional side view of the aspiration catheter being drawn into the guide catheter to remove the obstruction from the vasculature while the expandable member surrounds the obstruction, which is being suctioned by the aspiration catheter, in accordance with one or more embodiments of the present disclosure.

FIG. 4F further illustrates a cross-sectional side view of the aspiration catheter being drawn into the guide catheter to remove the obstruction from the vasculature while the expandable member surrounds the obstruction, which is being suctioned by the aspiration catheter, in accordance with one or more embodiments of the present disclosure.

DETAILED DESCRIPTION

Reference will now be made in detail to the subject matter disclosed, which is illustrated in the accompanying drawings.

Figure 1A:
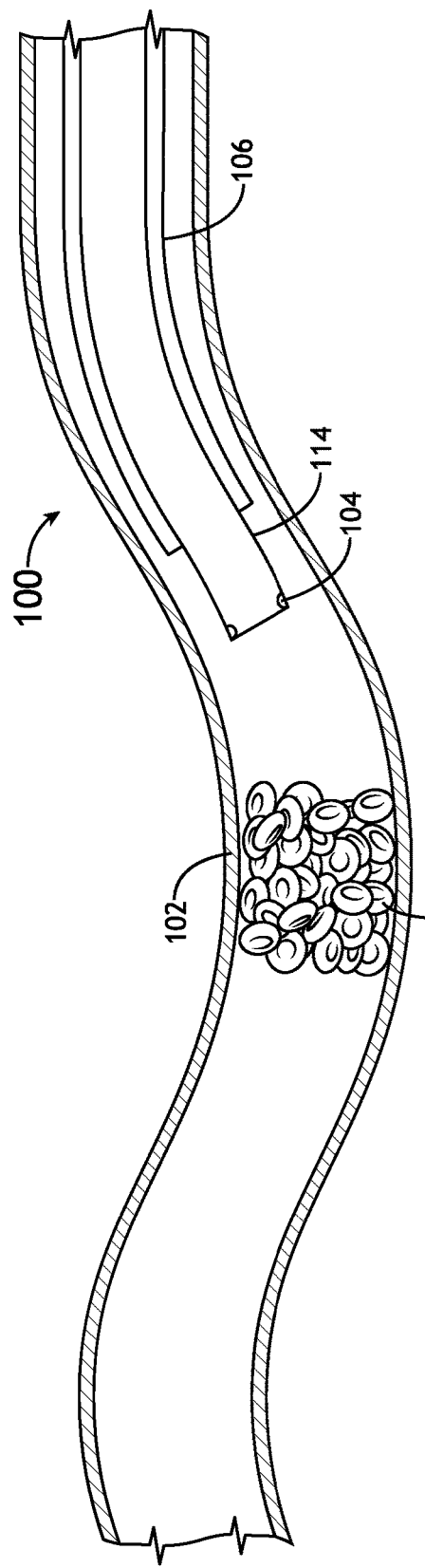
FIG. 1A illustrates a cross-sectional side view of one or more catheters of an obstruction removal system deployed within a vasculature, in accordance with one or more embodiments of the present disclosure.
Figure 1B:
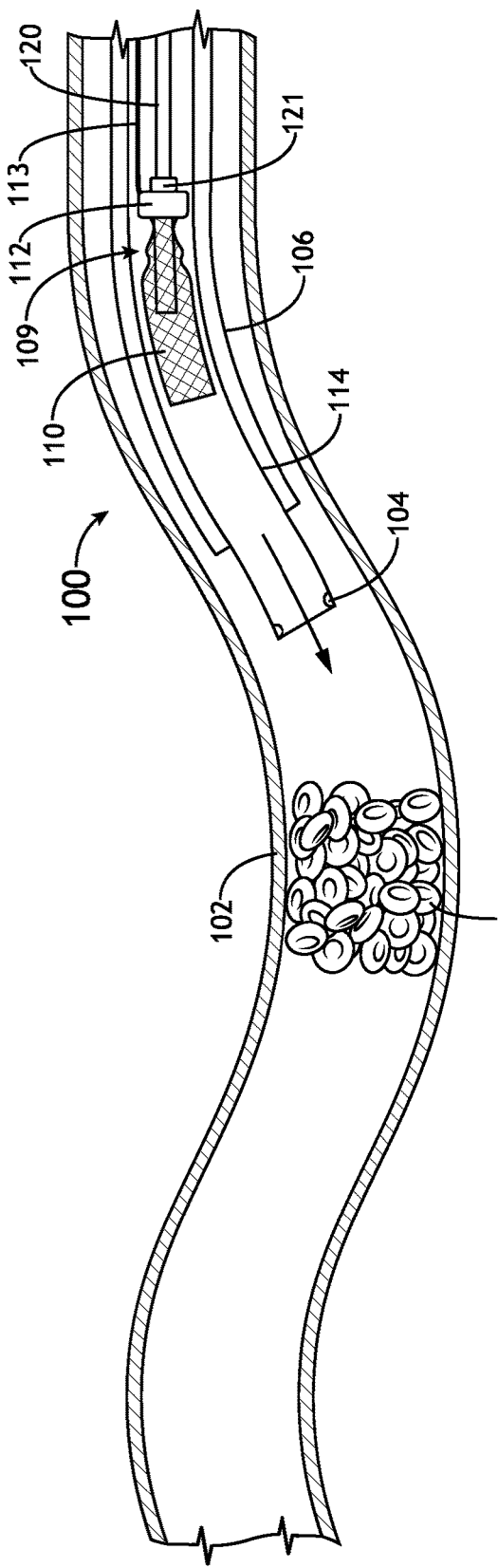
FIG. 1B illustrates a cross-sectional side view of an obstruction removal device of the obstruction removal system being deployed through a catheter, wherein the obstruction removal device is pushed through the catheter by a delivery wire/tube, in accordance with one or more embodiments of the present disclosure.
Figures 1C, 1D:
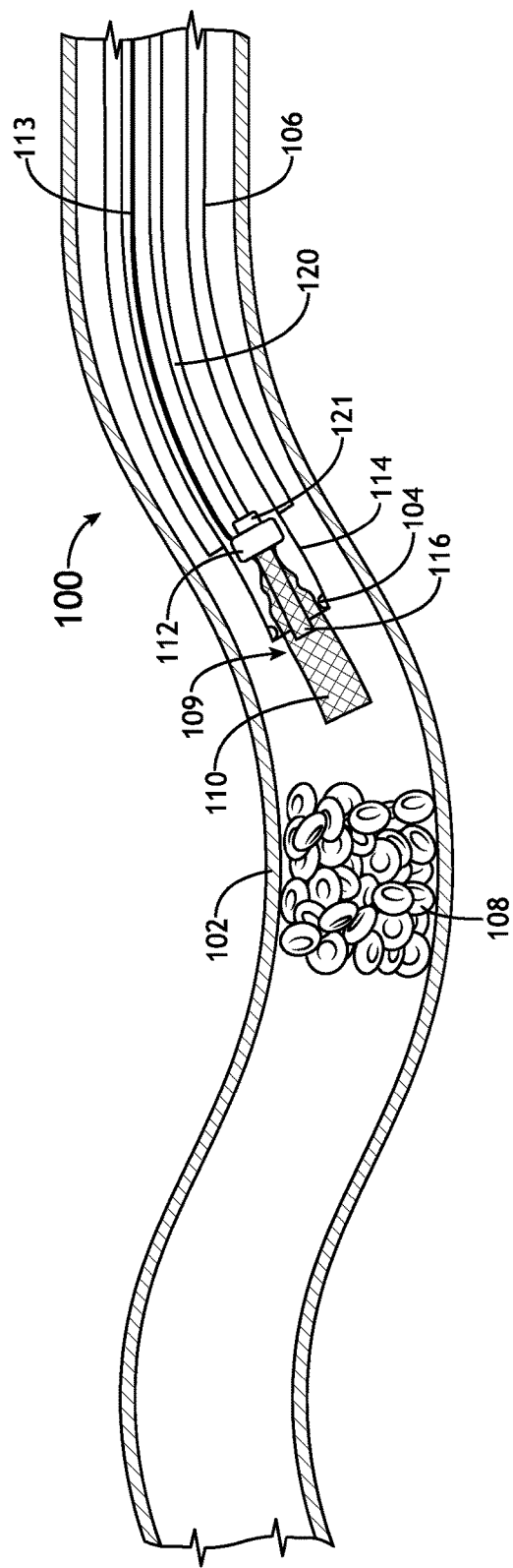
FIG. 1C illustrates a cross-sectional side view of the obstruction removal device being deployed through the catheter, wherein the obstruction removal device is pushed through the catheter by a delivery wire/tube, in accordance with one or more embodiments of the present disclosure.
FIG. 1D illustrates a cross-sectional side view of the obstruction removal device being deployed through the catheter, wherein the obstruction removal device is pushed through the catheter by the delivery wire/tube until a base member of the obstruction removal device reaches one or more guide stops, in accordance with one or more embodiments of the present disclosure.
Figure 1I:
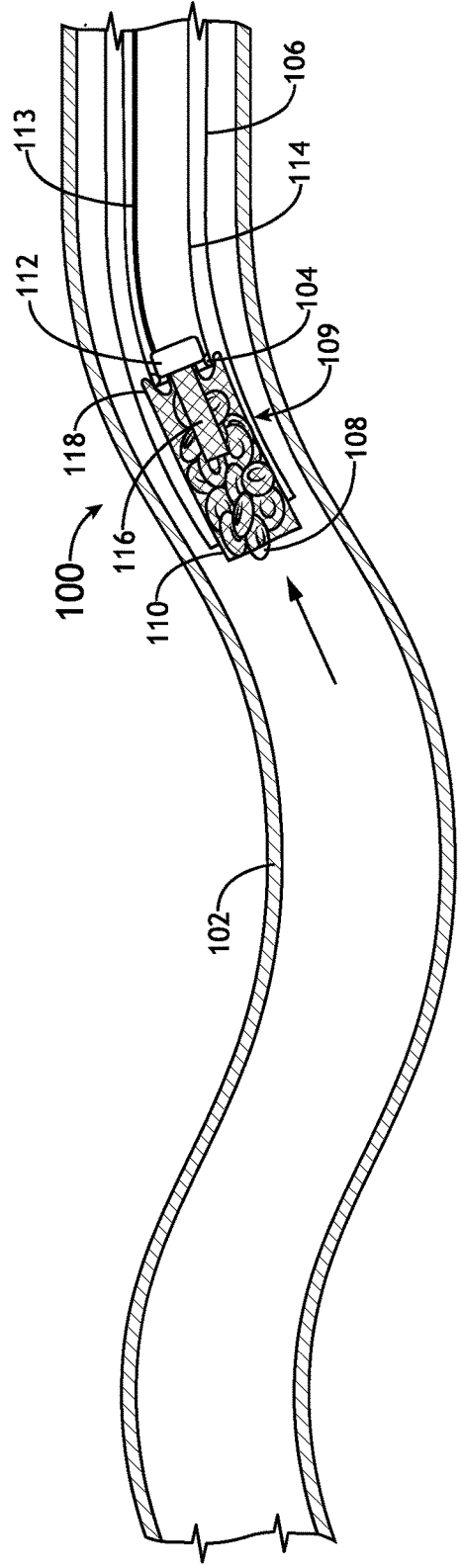
FIG. 1I illustrates a cross-sectional side view of the obstruction removal device and the catheter being drawn into the guide catheter to remove the obstruction from the vasculature while the expandable member surrounds the obstruction as the obstruction is being suctioned by the tubular member, in accordance with one or more embodiments of the present disclosure.
Figure 1J:
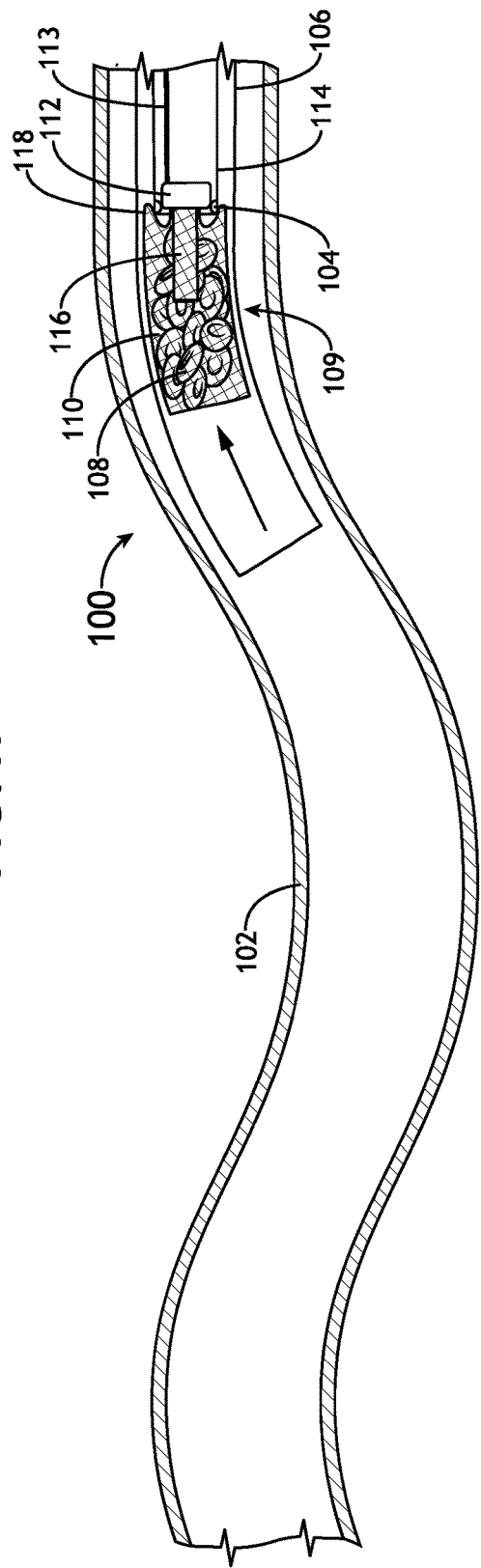
FIG. 1J illustrates a cross-sectional side view of the obstruction removal device and the catheter being pulled through the guide catheter to remove the obstruction from the vasculature while the expandable member surrounds the obstruction as the obstruction is being suctioned by the tubular member, in accordance with one or more embodiments of the present disclosure.
Figure 1M:
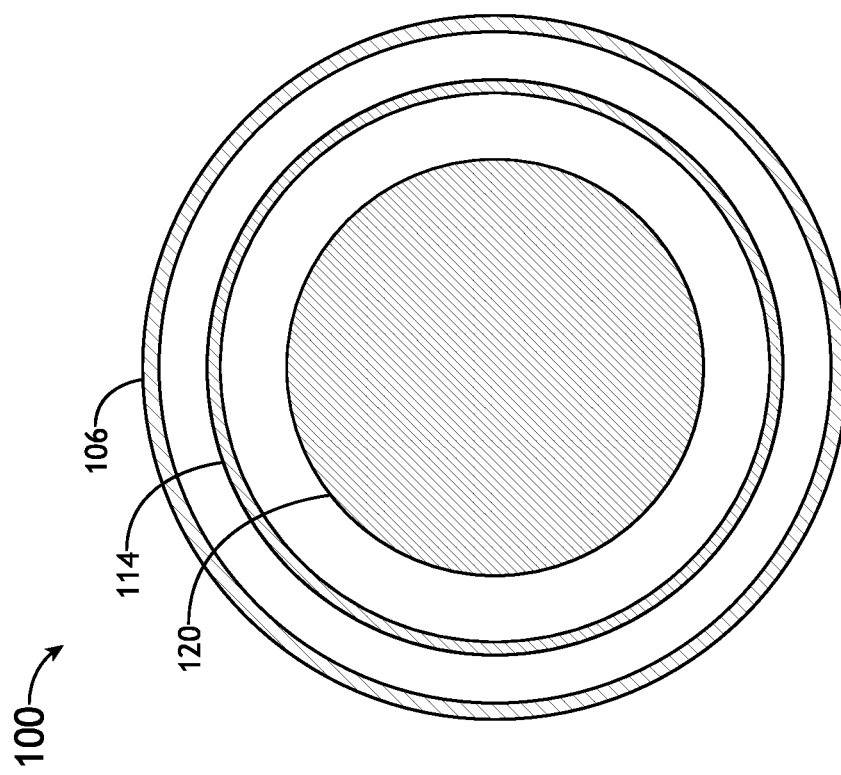
FIG. 1M illustrates a cross-sectional end view of a guide catheter with an aspiration catheter, intermediate catheter or microcatheter inserted within the guide catheter and a delivery tool inserted within the aspiration catheter, intermediate catheter or microcatheter, in accordance with one or more embodiments of the present disclosure.
Figure 1N:
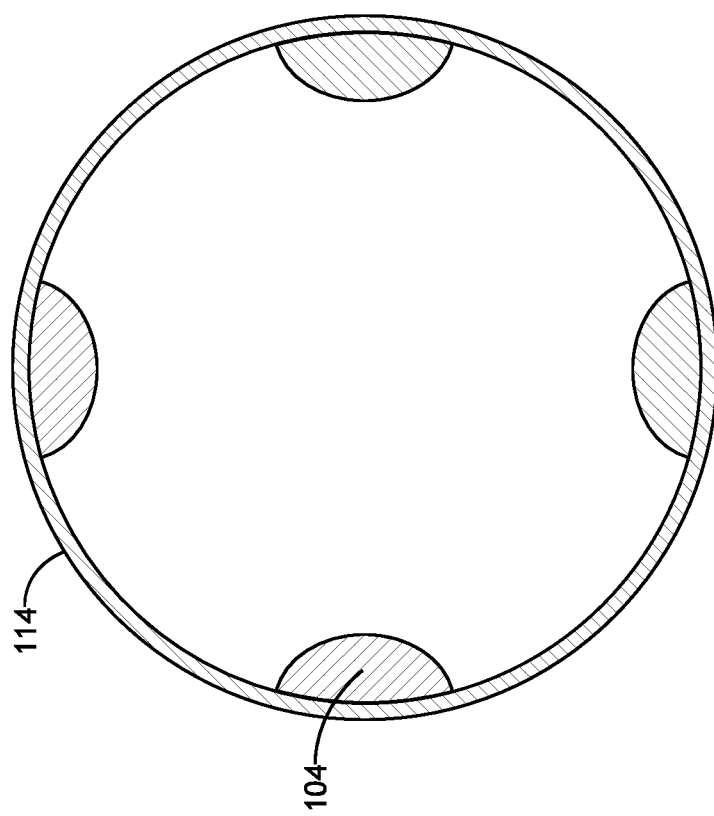
FIG. 1N illustrates a cross-sectional end view of aspiration catheter, intermediate catheter or microcatheter with guide stops attached to an inner surface of the aspiration catheter, intermediate catheter or microcatheter, in accordance with one or more embodiments of the present disclosure.
Figure 10:
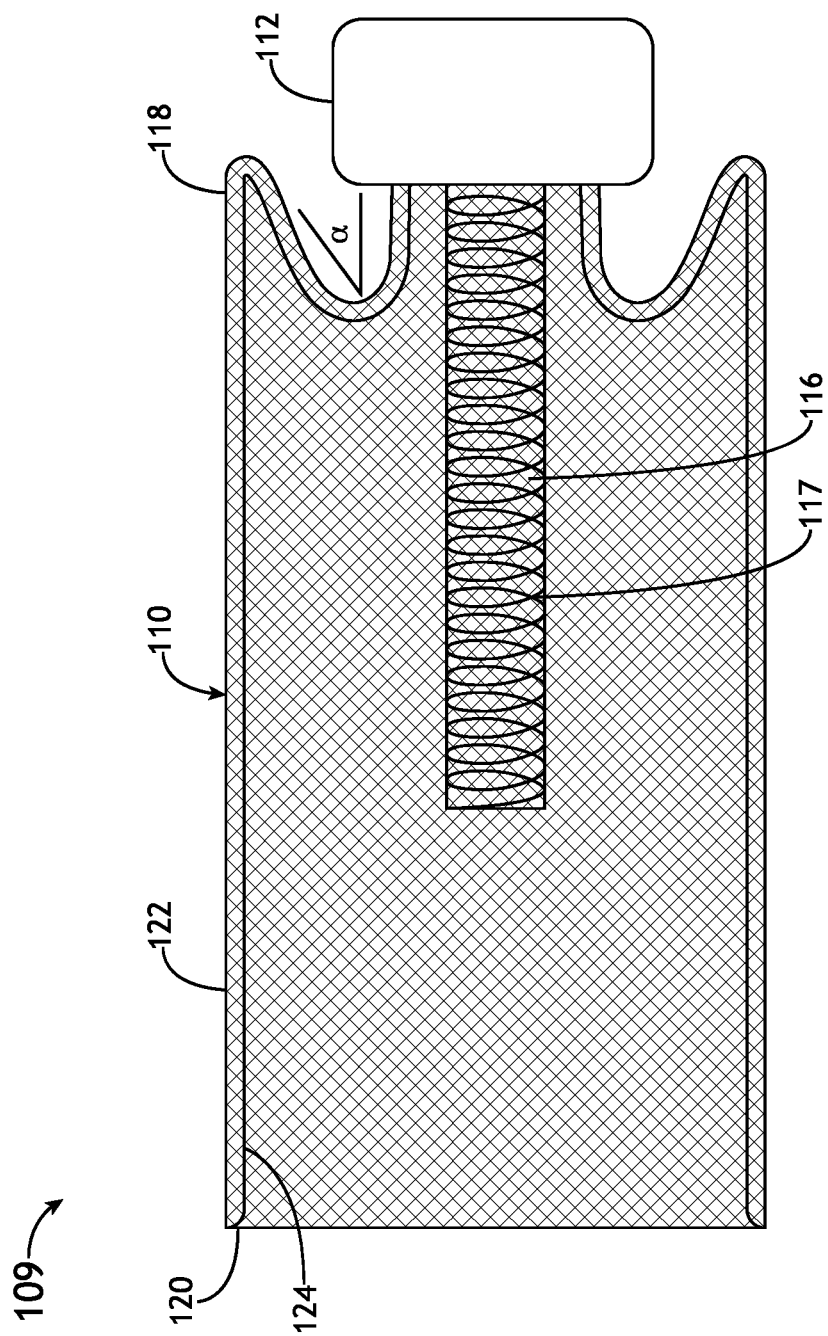
Figure 1P:
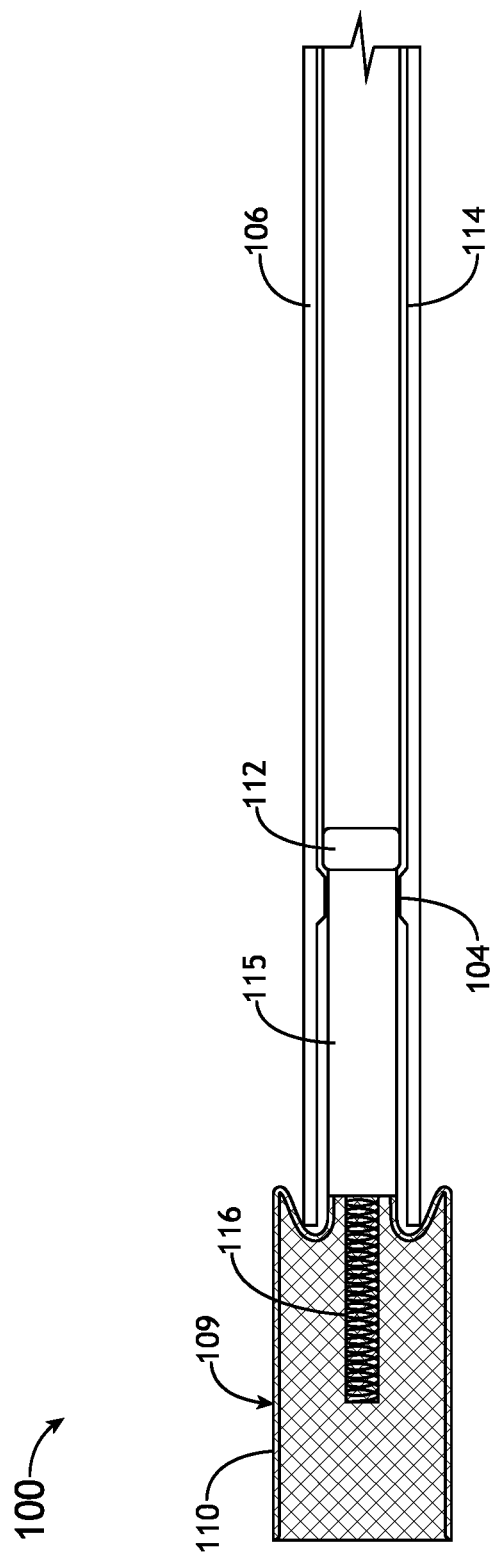
FIG. 1P illustrates a cross-sectional side view of the obstruction removal device deployed through a catheter, wherein the one or more guide stops are implemented by an indented or tapered portion of the catheter having a smaller cross-sectional area than other portions (e.g., upstream portions) of the catheter, in accordance with one or more embodiments of the present disclosure.

Referring now to FIGS. 1A through 1P, an obstruction removal system is described, in accordance with one or more embodiments of this disclosure. In particular, FIGS. 1A through 1P illustrate embodiments of an obstruction removal system configured to deploy an obstruction removal device including an expandable member within a vasculature to reduce the risks associated with removal of an obstruction when the obstruction is suctioned into and/or pulled through a catheter to remove the obstruction from the vasculature. The expandable member may be used to prevent an obstruction from passing to a potentially more dangerous area (e.g., causing a total blockage, blocking a portion of a vital vasculature, etc.). In this regard, a physician may determine whether an obstruction is prone to risk and selectively deploy the expandable member. Furthermore, the physician may deploy the expandable member at various locations away from the obstruction (e.g., clot), as needed.

In embodiments, the obstruction removal system includes a catheter configured to be inserted within a vasculature. The catheter may have one or more guide stops located at a distal end of the catheter. The obstruction removal system further includes an obstruction removal device that is configured to be inserted through the catheter and at least partially extended into the vasculature from the distal end of the catheter.

The obstruction removal device includes a base member configured to engage the one or more guide stops at the distal end of the catheter. In embodiments, the obstruction removal device further includes a tubular member coupled to the base member and configured to apply a suction force from the catheter to an obstruction to remove the obstruction from the vasculature. The obstruction removal device further includes an expandable member surrounding the tubular member. The expandable member is configured to transition from a contracted state to an expanded state after the expandable member is at least partially extended into the vasculature from the distal end of the catheter. The expandable member is further configured to at least partially surround the obstruction as the obstruction is being removed from the vasculature. In this manner, the expandable member helps prevent the obstruction (or portions thereof) from being dislodged into the vasculature.

FIGS. 1A through 1P illustrate one or more embodiments of an obstruction removal system 100. As shown in FIG. 1A, the obstruction removal system 100 includes a catheter 114 (e.g., an aspiration catheter, intermediate catheter, or the like) configured to be inserted through a vasculature 102 to a position proximate to an obstruction 108. The obstruction removal system 100 may include guide stops 104 attached (e.g., mounted) to or formed on an inner surface of the catheter 114, at or near a distal end of the catheter 114 (e.g., near an opening of the catheter). The obstruction removal system 100 may further include a guide catheter 106 configured to be inserted through the vasculature 102 before catheter 114 so that catheter 114 can be fed through the guide catheter 106.

In embodiments, the catheter 114 is configured to remove the obstruction 108 from the vasculature 102 when a suction force is applied to the catheter 114. For example, the catheter 114 may be coupled to a pump, syringe, vacuum chamber, or any other suction device configured to selectively produce negative pressure in the catheter 114 so that the obstruction 108 is drawn into (and/or suctioned onto) the catheter 114 to remove the obstruction 108 from the vasculature 102.

As shown in FIG. 1B, the obstruction removal system 100 further includes an obstruction removal device 109 including an expandable member 110. In a contracted state, the expandable member 110 is configured to be inserted through the catheter 114 and extended out of a distal opening of the catheter 114. When the expandable member 110 is in the contracted state, the expandable member 110 may fit through the guide stops 104. In FIG. 1B, the expandable member 110 is illustrated in an orientation where the funnel/basket opening is forward facing while the expandable member 110 is being fed through the catheter 114. However, in other configurations, the expandable member 110 may be inserted through the catheter 114 in an inverted orientation (where the funnel/basket opening trails behind). In such cases, the expandable member 110 will invert so that the funnel/basket opening is forward facing later on in the process. For example, the expandable member 110 may invert to look as it does in the drawings when the expandable member 110 is pulled back to remove the obstruction 108 from the vasculature 102 (i.e., during the steps illustrated in FIGS. 1G through 1J).

FIG. 1C illustrates the expandable member 110 deployed out of the distal opening of the catheter 114, where a base member 112 attached to the expandable member 110 is pushed up against, mated with, or otherwise engages the guide stops 104. The delivery tool 120 can then be removed (e.g., withdrawn) from the catheter 114/vasculature 102. A delivery tool 120 (e.g., a guide wire or tube) may be used to push the obstruction removal device 109 with the expandable member 110 through the catheter 114. In some embodiments, the delivery tool 120 may include an end-mounted support member 121 configured to support the obstruction removal device 109 as the obstruction removal device 109 is pushed through the catheter 114.

FIGS. 1D through 1F illustrate the expandable member 110 of the obstruction removal device 109 transitioning to an expanded state. In the expanded state, the expandable member 110 may form a basket with a first (proximal) opening that leads into the catheter 114 and a second (distal) opening that is configured to surround the obstruction 108 while the obstruction 108 is being suctioned into the catheter 114 to remove the obstruction 108 from the vasculature 102. In this regard, the second (distal) opening is larger than the first (proximal) opening.

It is to be understood that the use of guide stops 104 on an inner portion of a catheter 114 may be suitable to allow a physician to selectively position the obstruction removal device 109 relative to the obstruction 108 by translating some portion of the catheter 114 and/or the delivery tool 120. When positioning the catheter 114 and the obstruction removal device 109, the physician may account for such things as vasculature geometry, obstruction size, blood pressure, blood flow direction, or vasculature tissue strength. For example, in some instances, it may be undesirable to deploy the obstruction removal device 109 near the obstruction location (e.g., due to a complex vasculature structure) but may still be desirable to use the obstruction removal device 109 (e.g., to reduce/control debris separated from the obstruction 108 when the obstruction is being removed from the vasculature 102). In this regard, the obstruction removal device 109 may be deployed away from the obstruction 108 and still retain the benefit of reducing complications that may be caused by dislodgement or breaking up of the obstruction 108.

In embodiments, the obstruction removal device 109 further includes a tubular member 116 coupled to the base member 112 and configured to apply a suction force from the catheter 114 to an obstruction 108 to remove the obstruction 108 from the vasculature 102. The expandable member 110 surrounds the tubular member 116 and is configured to transition from a contracted state to an expanded state after the expandable member 110 is at least partially extended into the vasculature 102 from the distal end of the catheter 114. Thus, the expandable member 110 is configured to at least partially surround the obstruction 108 as the obstruction 108 is being removed from the vasculature 102. In this manner, the expandable 110 member helps prevent the obstruction 108 (or portions thereof) from being dislodged into the vasculature 102.

The tubular member 116 can be placed into contact with (or in close proximity of) the obstruction 108 so that the obstruction 108 can be suctioned into the catheter 114 via the tubular member 116. In some cases, the obstruction 108 (or a portion thereof) may be too hard to suction into the catheter 114; as a result, the obstruction 108 may become stuck onto the distal end of the tubular member 116 (e.g., as shown in FIG. 1G). When this occurs, the catheter 114 carrying the obstruction removal device 109 and obstruction 108 at its distal end can be pulled out of the vasculature 102 through the guide catheter 106 to remove the obstruction 108 from the vasculature 102. As shown in FIGS. 1H through 1J, the suction force holds the obstruction 108 to the distal end of the tubular member 116 while the expandable member 110 surrounds the obstruction 108 so that the obstruction 108 can be safely pulled through the guide catheter 106 without dislodging or releasing any debris into the vasculature 102.

As shown in FIGS. 1K and 1L, when the obstruction 108 is soft enough, the suction force will cause portions 107 of the obstruction 108 to break off or deform so that the obstruction 108 (or a portion thereof) is suctioned out of the vasculature 102 through the catheter 114. In some cases, the obstruction 108 can be fully aspirated. In other cases, part of the obstruction 108 may be aspirated and the remainder of the obstruction 108 may be removed by pulling the catheter 114 carrying the obstruction removal device 109 and obstruction 108 at its distal end through the guide catheter 106 to remove the obstruction 108 from the vasculature 102, as described above with reference to FIGS. 1G through 1J.

In some embodiments, the obstruction removal device 109 may have a wire 113 coupled to the base member 112 and extended all the way through the catheter 114. This wire 113 can prevent the obstruction removal device 109 from being unintentionally ejected from the distal end of the catheter 114 should the base member 112 become disengaged from the guide stops 104. The wire 113 can also be used to withdraw the obstruction removal device 109 from the vasculature 102 (i.e., by pulling the wire 113 to remove the obstruction removal device 109 by pulling it through the catheter 114).

FIG. 1M illustrates a cross-sectional end view of an obstruction removal system, where the delivery tool 120 is inserted through catheter 114 and guide catheter 106, and FIG. 1N illustrates a cross-sectional end view of the catheter 114 with guide stops 104 (e.g., one or more protrusions or a ring) attached to an inner surface of the catheter 114. The depicted guide stops 104 are non-limiting examples of means for engaging a base member. Additional structures or geometries may be used without deviating from the scope of this disclosure. The guide stops 104 may be configured to engage with the base member 112 attached to the expandable member 110 (e.g., by taking up a portion of the cross-sectional area of the catheter 114). Additionally, the guide stops 104 may be configured to take up a minimal cross-sectional area of the catheter 114, in order to allow injection of radioactive dye. In some embodiments, the guide stops 104 may be further configured to mate with the base member 112 to temporarily lock it in place at the distal end of the catheter 114.

Referring now to FIG. 1P, in some embodiments, the one or more guide stops 104 may be implemented by an indented or tapered portion of the catheter 114. For example, the indented/tapered portion 104 may have a smaller cross-sectional area than other portions (e.g., upstream portions) of the catheter 114. In an example embodiment, the indented/tapered portion 104 may have a diameter of 0.067 inches, while a majority of the catheter has a diameter of 0.071 inches, and the base member 112 (e.g., a marker band) has a diameter of 0.069 inches. These values are provided as examples to show that the difference in diameter may be as small as a difference of 0.001 to 0.01 inches; however, other values/ranges may be appropriate.

In some embodiments, the indented/tapered portion 104 (or other guide stops 104) may be located at a distance from the distal end of the catheter 114. For example, the distance from the distal end of the catheter 114 may be in the range of 5 cm to 30 cm. To accommodate this distance, the obstruction removal device 109 may include an intermediate portion 115 between the base member 112 and the expandable member 110. In some embodiments, the intermediate portion 115 is part of the tubular member 116. For example, the tubular member 116 may have a length greater than the distance between the indented/tapered portion 104 (or other guide stops 104) and the distal end of the catheter 114. In other embodiments, the intermediate portion 115 is formed by another tubular member or a substantially tubular section of braid/mesh. If a braid/mesh is used, the braid/mesh may be formed from the same material as the expandable member 110; however, other materials (e.g., steel) may be used to reduce cost and/or achieve desired structural attributes (e.g., strength, flexibility, rigidity, etc.).

Referring generally to embodiments of the obstruction removal system 100 disclosed herein, the expandable member 110 may be configured to transition between a first configuration and a second configuration, or between a contracted state and an expanded state, in any number of ways, including, but not limited to, unsheathing (e.g., extension through catheter 114), disengagement of locking members (e.g., wires, hooks, etc.) attached to the expandable member 110, use of shape memory alloys (e.g., Nitinol), or the like. It is envisioned that when the expandable member is in an expanded state, the expandable member may take up a substantial portion (e.g., 80% or more) of the cross-section of the vasculature 102.

In embodiments, the expandable member 110 may comprise a wire mesh. Such a wire mesh may include wires made of a flexible material (e.g., nitinol, cobalt chromium, polymer mesh, or the like), where the wires (e.g., 16 to 288 or more wires), have a certain diameter (e.g., from 0.0007 inches to 0.0050 inches), and have certain material properties (e.g., strength, coefficient of friction with blood, resistance to plastic deformation, etc.) suitable for engaging the obstruction 108. Furthermore, the wire mesh may include various sets of wires (e.g., support wires with larger diameters, wires to engage a vessel wall, wires to engage a portion of the obstruction or stentriever, radiopaque or radiodense wires, etc.).

FIG. 1O is a cross-sectional side view illustrating the obstruction removal device 109, in accordance with one or more embodiments of this disclosure. As noted above, the expandable member 110 forms a basket at the distal end of the catheter 114 after transitioning from a contracted state to an expanded state. The basket surrounds the tubular member 116 so that the obstruction 108 is at least partially captured within the basket when the obstruction 108 is being suctioned into the catheter 114 and/or held against the tubular member 116 by the suction force. The wire mesh that forms the expandable member 110 may be folded over itself at a distal edge 120 of the basket to form an outer layer 122 and an inner layer 124 that are bound together at the base member 112. Folding the wire mesh over itself at the distal edge 120 of the basket may help prevent stray wires that can snag on the vessel wall or cause damage the vasculature 102. In embodiments, the base member 112 may comprise an annular fitting (made from a molded structure or another mesh). Alternatively, the base member 112 can also be formed from a folded or rolled up a portion of the wire mesh.

A proximal portion 118 of the expandable member 110 may be configured to fold over the distal end of the catheter 114 in order to prevent the expandable member 110 from being suctioned into the catheter 114. In some embodiments, the expandable member 110 includes a narrow fold angle α between the proximal (smaller) opening of the basket and the proximal portion 118 of the basket. For example, the fold angle α may be in the range of 0 to 90 degrees, or possibly narrower (e.g., 0 to 45 degrees). Having a narrow fold angle α can help prevent the expandable member 110 from being unintentionally suctioned into the catheter 114 when the obstruction 108 is being aspirated.

In embodiments, the tubular member 116 may be a flexible polymer tube; however, other tubing (e.g., a metal/glass tube) may also be appropriate. The tubular member 116 may be structurally reinforced by a coil 116 or by wire mesh. In other embodiments, the tubular member 116 itself may be formed from wire mesh with sufficient density to maintain appropriate suction.

In some embodiments, the entire mesh or at least one of the layers (e.g., the outer layer 122 and/or the inner layer 124) may have a mesh density selected to prevent or reduce fluid flow through the wire mesh (i.e., through layers/walls of the funnel). In other embodiments, the expandable member 110 may alternatively, or additionally, include a membrane (e.g., a polymer membrane, or the like) disposed upon at least one of the layers (e.g., the outer layer 122 and/or the inner layer 124) to prevent or reduce fluid flow through the wire mesh (i.e., through layers/walls of the funnel). In some embodiments, a membrane may be disposed between the outer layer 122 and the inner layer 124 of the funnel. In some embodiments, the membrane covers at least half (e.g., 50% to 100%) of the outer layer 122 and/or the inner layer 124. In other embodiments, the membrane substantially covers (e.g., covers 80% to 100%) of the outer layer 122 and/or the inner layer 124.

Any number of the presently disclosed elements may be suitable for imaging by a non-invasive imaging technology (e.g., X-ray, CT scans, etc.). For instance, the obstruction removal device 109 (or any portion thereof), guide catheter 106, catheter 114, delivery tool 120, and/or any additional components of the obstruction removal system 100 may comprise radiodense or radiopaque material (e.g., titanium, tungsten, barium sulfate, or zirconium oxide) suitable for insertion in a human body.

It is to be understood that any number of components of the obstruction removal system 100 may be attached by any suitable means including, but not limited to, welding, adhesive, mechanical fastening, interference fittings, etc. For example, the base member 112 may be attached to the expandable member 110 by such means. Alternatively, or additionally, two or more of the components may be portions of a common structure (e.g., a common mold, print, or mesh structure).

In some embodiments, the obstruction removal device 109 is temporarily attached to the delivery tool 120. For example, the obstruction removal device 109 may be configured to detach from the delivery tool 120 after base member 112 engages the one or more guide stops 104.

The base member 112 and guide stop(s) 104 may be configured to selectively engage and disengage. It is envisioned that the ability to selectively engage and disengage may provide advantages. For example, the ability to selectively disengage may allow for reusability of one or more of the components (e.g., obstruction removal device 109, delivery tool 120, catheter 114, etc.). By way of another example, the ability to engage and disengage may provide increased functionality when inserting and removing components through the catheter 114 (e.g., fewer components translating through the catheter 114 at the same time).

It is envisioned that there may be multiple orders in which one or more devices of the obstruction removal system 100 are deployed. Factors for determining an order may include, but are not limited to, vasculature properties (e.g., vasculature size, vasculature geometries, branches of the vasculature, vasculature wall strength, etc.), blood pressure, blood flow direction, duration of operation (i.e., does patient require a reduced operating time for safety concerns), size of obstruction, or the configuration of the obstruction removal device.

Referring generally to FIGS. 1A through 1L, a method of removing an obstruction 108 from a vasculature 102 may include, but is not limited to, the steps of: inserting a catheter 114 within a vasculature 102, the catheter 114 having one or more guide stops 104 located at a distal end of the catheter 114 (FIG. 1A); inserting an obstruction removal device 109 through the catheter 114 and at least partially extending the obstruction removal device 114 into the vasculature 102 from the distal end of the catheter 114, the obstruction removal device 109 including a base member 112 that engages the one or more guide stops 104 at the distal end of the catheter 114, the obstruction removal device 109 further including an expandable member 110 and a tubular member 116 (FIGS. 1B and 1C); transitioning the expandable member 110 from a contracted state to an expanded state after the expandable member 110 is at least partially extended into the vasculature 102 from the distal end of the catheter 114 (FIGS. 1D and 1E); and applying a suction force from the catheter 114 to an obstruction 108, via the tubular member 116, to remove the obstruction 108 from the vasculature 102, wherein the expandable member 110 at least partially surrounds the obstruction 108 as the obstruction 108 is being removed from the vasculature 102 (FIG. 1F and FIGS. 1K and 1L and/or FIGS. 1G through 1J). In implementations, the system 100 can be used in stages based on the situational requirements. For example, if aspiration fails or if only a portion of the obstruction 108 can be suctioned through the tubular member 116/catheter 114 (FIGS. 1K and 1L), then the obstruction 108 or remainder of the obstruction 108 may be removed by pulling the catheter 114 carrying the obstruction removal device 109 and obstruction 108 at its distal end through the guide catheter 106 to remove the obstruction 108 from the vasculature 102, as described above with reference to FIGS. 1G through 1J.

Referring now to FIGS. 2A through 2M, an obstruction removal system is described, in accordance with one or more additional embodiments of this disclosure. In particular, FIGS. 2A through 2M illustrate embodiments of an obstruction removal system configured to deploy an expandable member in a vasculature to reduce the risks associated with removal of an obstruction when the obstruction is suctioned into the catheter to remove the obstruction from the vasculature. The expandable member may be used to prevent an obstruction from passing to a potentially more dangerous area (e.g., causing a total blockage, blocking a portion of a vital vasculature, etc.). In this regard, a physician may determine whether an obstruction is prone to risk and selectively deploy the expandable member. Furthermore, the physician may deploy the expandable member at various locations away from the obstruction (e.g., clot), as needed.

In embodiments, the obstruction removal system includes a catheter configured to be inserted within a vasculature. In embodiments, the obstruction removal device further includes a tubular member configured to apply a suction force from the catheter to the obstruction to remove the obstruction from the vasculature. The expandable member surrounds the tubular member and is configured to transition from a contracted state to an expanded state after the expandable member is at least partially extended into the vasculature from the distal end of the catheter. The expandable member is further configured to at least partially surround the obstruction as the obstruction is being removed from the vasculature.

Figure 2G:
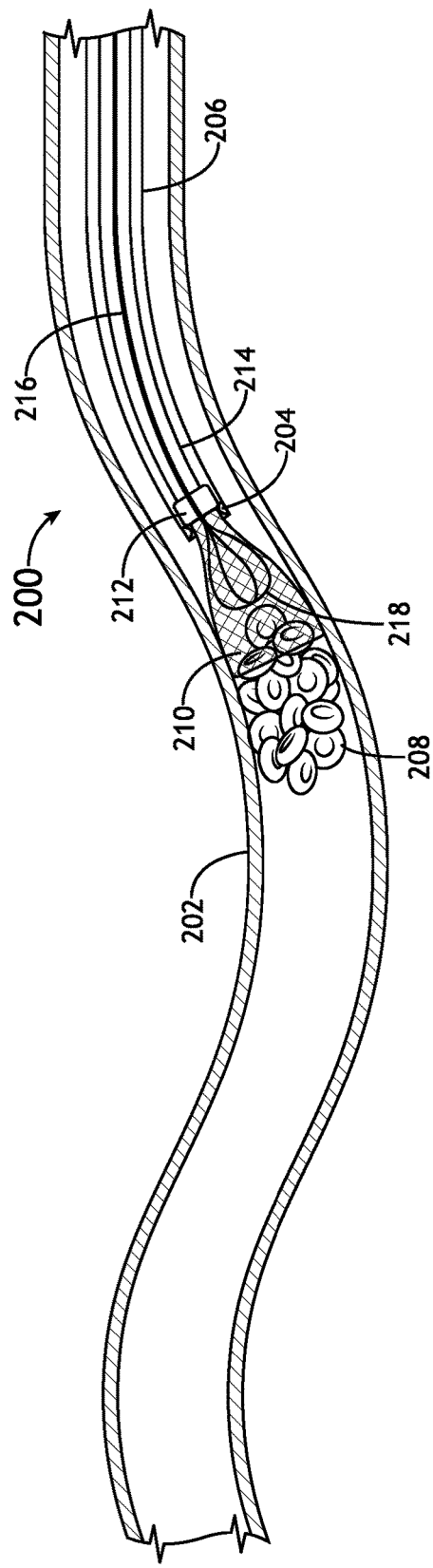
FIG. 2G illustrates a cross-sectional side view of the obstruction removal system deployed within the vasculature, wherein a suction force is applied to the catheter to draw the obstruction through the expandable member into the catheter, in accordance with one or more embodiments of the present disclosure.

FIGS. 2A through 2M illustrate one or more embodiments of an obstruction removal system 200. As shown in FIG. 2A, the obstruction removal system 200 includes a catheter 206 (e.g., an aspiration catheter, guide catheter, intermediate catheter, or the like) configured to be inserted through a vasculature 202 to a position proximate to an obstruction 208. The obstruction removal system 200 may include guide stops 204 attached (e.g., mounted) to or formed on an inner surface of the catheter 206, at or near a distal end of the catheter 206 (e.g., near an opening of the catheter).

In embodiments, the catheter 206 is configured to remove the obstruction 208 from the vasculature 202 when a suction force is applied to the catheter 206. For example, the catheter 206 may be coupled to a pump, syringe, vacuum chamber, or any other suction device configured to selectively produce negative pressure in the catheter 206 so that the obstruction 208 is drawn into the catheter 206 to remove the obstruction 208 from the vasculature 202.

As shown in FIG. 2B, the obstruction removal system 200 further includes an expandable member 210. In a contracted state, the expandable member 210 is configured to be inserted through the catheter 206 and extended out of a distal opening of the catheter 206. When the expandable member 210 is in the contracted state, the expandable member may fit through the guide stops 204.

FIG. 2C illustrates the expandable member 210 deployed out of the distal opening of the catheter 206, where a base member 212 attached to the expandable member 210 is pushed up against, mated with, or otherwise engages the guide stops 204. A delivery tool 220 (e.g., a guide wire or tube) may be used to push the expandable member 210 through the catheter 206. In some embodiments, the delivery tool 220 may include an end-mounted support member 221 configured to support the expandable member 210 as the expandable member 210 is pushed through the catheter 206.

FIG. 2D illustrates the expandable member 210 transitioned to an expanded state. The delivery tool 220 can then be removed (e.g., withdrawn) from the catheter 206/vasculature 202. In the expanded state, the expandable member 210 may form a funnel with a first (proximal) opening that leads into the catheter 206 and a second (distal) opening that is configured to receive the obstruction 208 when the obstruction 208 is being suctioned into the catheter 206 to remove the obstruction 208 from the vasculature 202. In this regard, the second (distal) opening is larger than the first (proximal) opening.

It is to be understood that the use of guide stops 204 on an inner portion of a catheter 206 may be suitable to allow a physician to selectively position the expandable member 210 at an appropriate distance from an obstruction 208 by translating some portion of the catheter 206 and/or the delivery tool 220. When positioning the catheter 206 and the expandable member 210, the physician may account for such things as vasculature geometry, obstruction size, blood pressure, blood flow direction, or vasculature tissue strength. For example, it may be undesirable to deploy the expandable member 210 near the obstruction location (e.g., due to a complex vasculature structure) but may still be desirable to use the expandable member 210 (e.g., to reduce/control debris separated from the obstruction 208 when the obstruction is being removed from the vasculature 202). In this regard, the expandable member 210 may be deployed away from the obstruction 208 and still retain the benefit of reducing complications that may be caused by dislodgement or breaking up of the obstruction 208.

Referring now to FIG. 2E, the obstruction removal system 200 may further include an agitator 218 configured to be inserted through the catheter 206. For example, the agitator 218 may be coupled or formed on/near a distal end of a delivery tool 216 (e.g., a guide wire or tube) configured to be inserted through the catheter 206. In some embodiments, the agitator 218 may be delivered through the catheter 206 using a microcatheter 214 (e.g., any suitable microcatheter or delivery tube). The microcatheter 214 may be used to contain the agitator 218 and keep the agitator 218 from expanding within the catheter 206. This may provide one or more advantages, such as, but not limited to, reducing friction between the agitator 218 and the catheter 206, permitting the agitator 218 to be inserted through the base member 212 and/or the distal opening of the catheter 206, and preventing the agitator 218 from prematurely engaging with the expandable member 210. Alternatively, the agitator 218 may be guided through the catheter 206 by advancing the delivery tool 216 without the use of a microcatheter 214.

FIG. 2F illustrates the agitator 218 inserted through the base member 212, the expandable member 210, and the distal opening of the catheter 206. The agitator 218 is attached to the delivery tool 216, so that actuation of the delivery tool 216 results in actuation of the agitator 218. For example, advancing or withdrawing the delivery tool 216 results in an advancement or withdrawal of the agitator 218, respectively. This may be performed manually, or alternatively, Alternatively, the delivery tool 216 may be coupled to a linear actuator configured to selectively actuate the delivery tool 216 forward and backward. In addition, the agitator 218 can be rotationally actuated (e.g., spun) by rotating the delivery tool 216 clockwise or counterclockwise about its longitudinal axis. The delivery tool 216 may be rotated manually (e.g., by spinning or twirling the delivery tool 216 between a user's fingers or by using a crank to rotate the delivery tool 216 about its longitudinal axis). Alternatively, the delivery tool 216 may be coupled to a rotational actuator (e.g., a motor or servo) configured to rotate the delivery tool 216 about its longitudinal axis.

In embodiments, the agitator 218 includes one or more wires configured into one or more loops, much like a mixer head (e.g., a whisk-like or eggbeater-like structure). Alternatively, or additionally, the agitator 218 may include one or more wires or prongs that form one or more of: a helical, spiral, or screw-like structure; a hook; a flat blade, a crossed blade, annular blade, or the like. In general, the agitator 218 may have any structure that can engage an obstruction 208 to break apart or separate the obstruction into pieces.

FIG. 2G illustrates the agitator 218 deployed out of the distal end of the catheter 206 while the obstruction 208 is being suctioned into the catheter 206. It is to be understood that there may be one or more methods for engaging the obstruction 208 with the agitator 218. For example, the agitator 218 may engage the obstruction 208 when the obstruction 208 is at least partially surrounded by the expandable member 210. Alternatively, the agitator 218 may be at least partially extended beyond the expandable member 210 to engage the obstruction 208 before the obstruction 208 enters the expandable member 210.

Figure 2H:
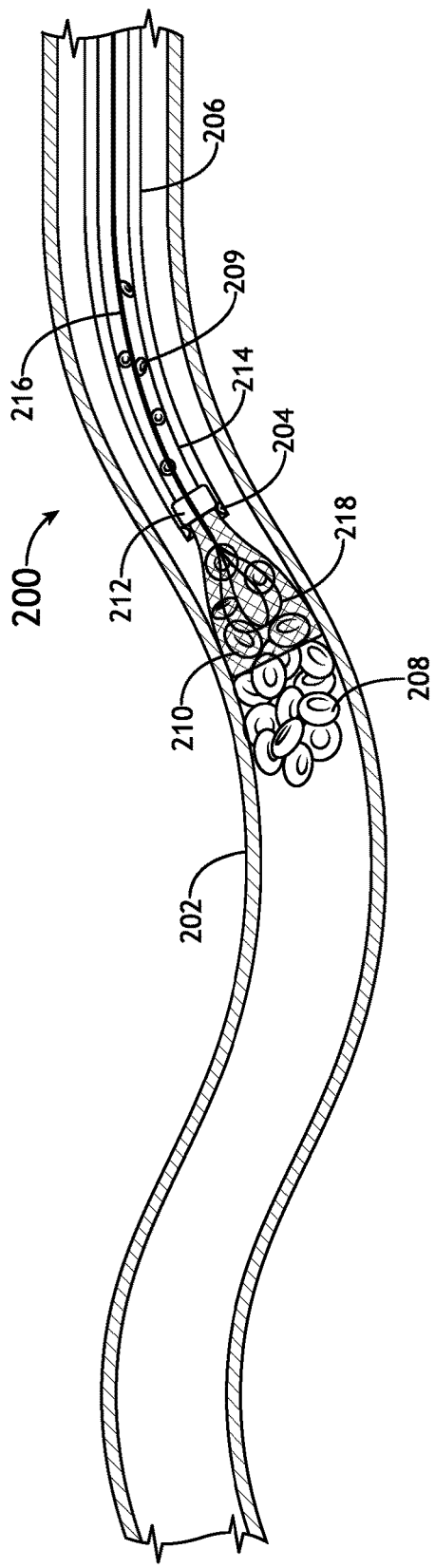
FIG. 2H illustrates a cross-sectional side view of the obstruction removal system deployed within the vasculature, wherein a suction force is applied to the catheter to draw the obstruction through the expandable member into the catheter, and wherein the agitator is used to break apart the obstruction as the obstruction is being suctioned through the expandable member into catheter to remove the obstruction from the vasculature, in accordance with one or more embodiments of the present disclosure.

As shown in FIG. 2H, the agitator 218 is used to break apart the obstruction 208 as the obstruction 208 is being suctioned, through the funnel formed by the expandable member 210, into catheter 206 to remove the obstruction 208 from the vasculature 202. Smaller pieces 209 of the obstruction 208 are then suctioned into the catheter 206 to remove the obstruction 208 from the vasculature 202.

In embodiments, the expandable member 210 may be configured to prevent contact between the agitator 218 and a vessel wall of the vasculature 202 when the agitator 218 is rotationally actuated (e.g., when the agitator is spinning). For example, the expandable member 210 and the agitator 218 may be configured to maintain a spatial relationship, wherein a widest portion of the agitator 218 is bound by the funnel formed by the expandable member 210 when the agitator 218 is rotationally actuated to prevent the agitator 218 from damaging the vasculature 202.

In some embodiments, the expandable member 210 has a wire (much like wire 113) coupled to the base member 212 and extended all the way through the catheter 206. This wire can prevent the expandable member 210 from being unintentionally ejected from the distal end of the catheter 206 should the base member 212 become disengaged from the guide stops 204. The wire can also be used to withdraw the expandable member 210 from the vasculature 202 (i.e., by pulling the wire to remove the expandable member 210 by pulling it through the catheter 206).

Figure 2J:
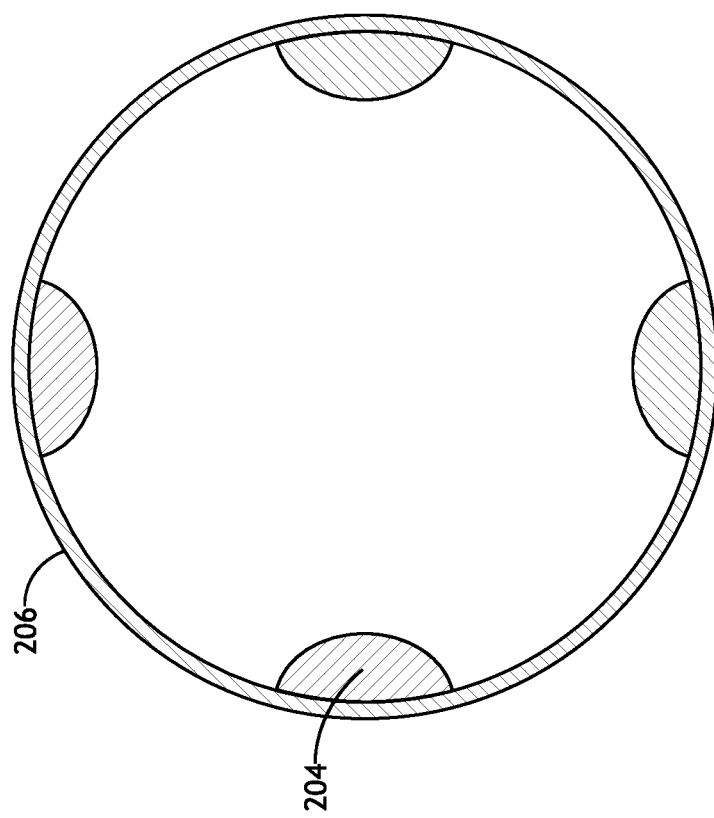
FIG. 2J illustrates a cross-sectional end view of a catheter with guide stops attached to an inner surface of the catheter, in accordance with one or more embodiments of the present disclosure.

FIG. 2I illustrates a cross-sectional end view of an obstruction removal system, where the delivery tool 216 is inserted through microcatheter 214 and catheter 206, and FIG. 2J illustrates a cross-sectional end view of the catheter 206 with guide stops 204 (e.g., one or more protrusions or a ring) attached to an inner surface of the catheter 206. The depicted guide stops 204 are non-limiting examples of means for engaging a base member. Additional structures or geometries may be used without deviating from the scope of this disclosure. The guide stops 204 may be configured to engage with the base member 212 attached to the expandable member 210 (e.g., by taking up a portion of the cross-sectional area of the catheter 206). Additionally, the guide stops 204 may be configured to take up a minimal cross-sectional area of the catheter 206, in order to allow injection of radioactive dye. In some embodiments, the guide stops 204 may be further configured to mate with the base member 212 to temporarily lock it in place at the distal end of the catheter 206.

Referring generally to embodiments of the obstruction removal system 200 disclosed herein, the expandable member 210 may be configured to transition between a first configuration and a second configuration, or between a contracted state and an expanded state, in any number of ways, including, but not limited to, unsheathing (e.g., extension through catheter 206), disengagement of locking members (e.g., wires, hooks, etc.) attached to the expandable member 210, use of shape memory alloys (e.g., Nitinol), or the like. It is envisioned that when the expandable member is in an expanded state, the expandable member may take up a substantial portion (e.g., 80% or more) of the cross-section of the vasculature 202.

In embodiments, the expandable member 210 may comprise a wire mesh. Such a wire mesh may include wires made of a flexible material (e.g., nitinol, cobalt chromium, polymer mesh, or the like), where the wires (e.g., 16 to 288 or more wires), have a certain diameter (e.g., from 0.0007 inches to 0.0050 inches), and have certain material properties (e.g., strength, coefficient of friction with blood, resistance to plastic deformation, etc.) suitable for engaging the obstruction 208 and/or the agitator 218. Furthermore, the wire mesh may include various sets of wires (e.g., support wires with larger diameters, wires to engage a vessel wall, wires to engage a portion of the obstruction or stentriever, radiopaque or radiodense wires, etc.).

Figure 2K:
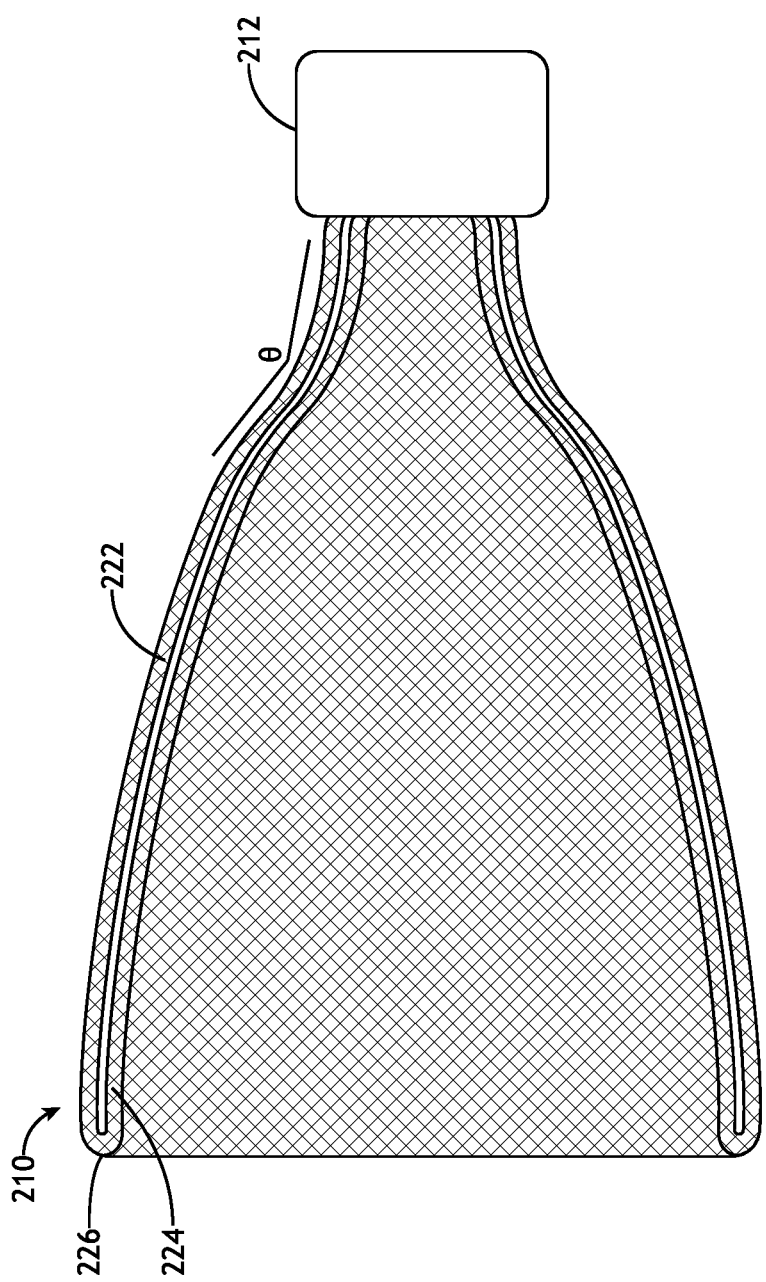
FIG. 2K illustrates a cross-sectional side view of the expandable member of the obstruction removal system, in accordance with one or more embodiments of the present disclosure.
Figure 2L:
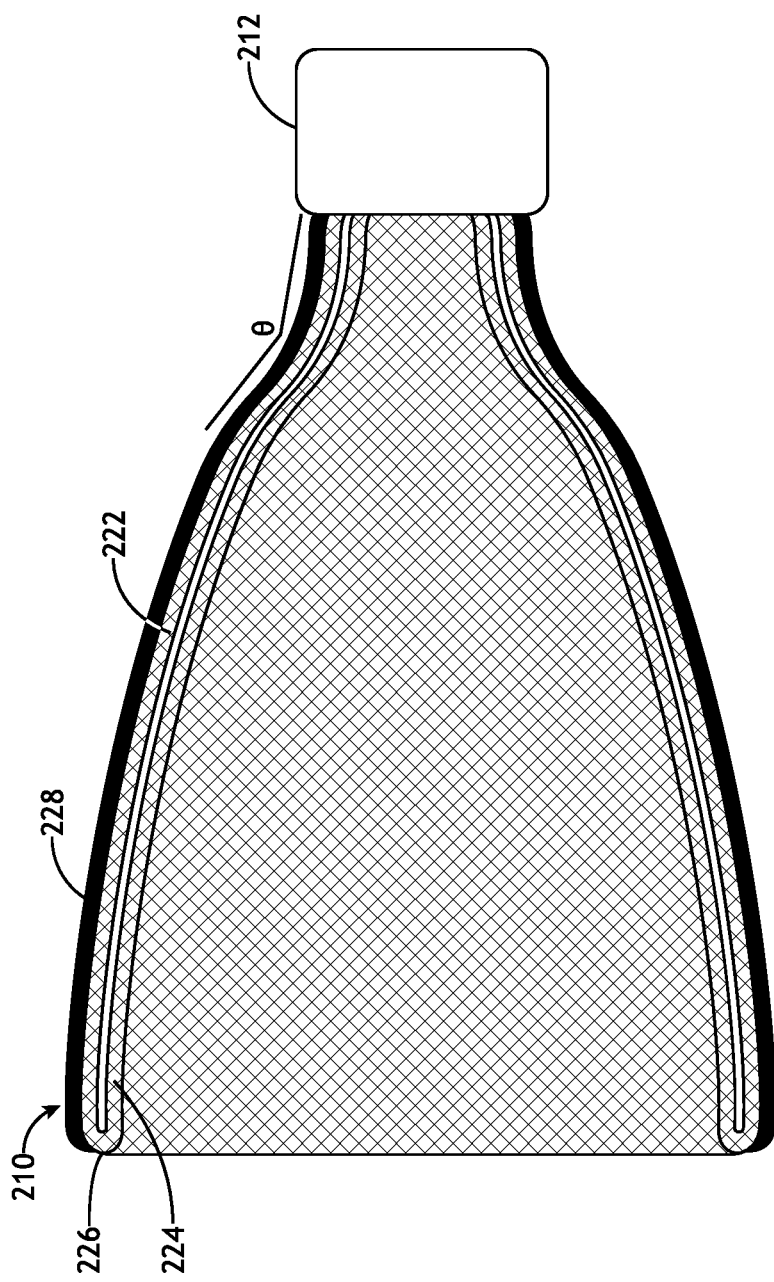
FIG. 2L illustrates a cross-sectional side view of the expandable member of the obstruction removal system, in accordance with one or more embodiments of the present disclosure.

FIGS. 2K through 2M are cross-sectional side views illustrating various embodiments of the expandable member 210. As noted above, the expandable member 210 forms a funnel at the distal end of the catheter 206 after transitioning from the contracted state to the expanded state. The wire mesh that forms the expandable member 210 may be folded over itself at a distal edge 226 of the funnel to form an outer layer 222 and an inner layer 224 that are bound together at the base member 212. Folding the wire mesh over itself at the distal edge 226 of the funnel may help prevent stray wires that can snag on the vessel wall or cause damage the vasculature 202. In embodiments, the base member 212 may comprise an annular fitting (made from a molded structure or another mesh). Alternatively, the base member 212 can also be formed from a fold or rolled up a portion of the wire mesh.

In some embodiments, the expandable member 210 includes a steep transition angle θ between the proximal (smaller) opening of the funnel and the distal (larger) opening of the funnel. For example, the transition angle θ may be in the range of 90 to 120 degrees. Having a steep transition angle θ can help prevent the expandable member 210 from being unintentionally suctioned into the catheter 206 when the obstruction 208 is being removed from the vasculature 202.

The entire mesh or at least one of the layers (e.g., the outer layer 222 and/or the inner layer 224) may have a mesh density selected to prevent or reduce fluid flow through the wire mesh (i.e., through layers/walls of the funnel). Otherwise, the funnel formed by the expandable member 210 may not produce enough suction force within the vasculature 202 to draw the obstruction 208 into the funnel and then into the catheter 206. In some embodiments, the entire mesh or at least one of the layers (e.g., the outer layer 222 and/or the inner layer 224) may have a wire mesh density in the range of 48 to 144 wires/braid.

As shown in FIGS. 2L and 2M, the expandable member 210 may alternatively, or additionally, include a membrane 222 (e.g., a polymer membrane, or the like) disposed upon at least one of the layers (e.g., the outer layer 222 and/or the inner layer 224) to prevent or reduce fluid flow through the wire mesh (i.e., through layers/walls of the funnel). For example, FIG. 2L illustrates an embodiment of the expandable member 210 with a membrane 228 disposed upon the outer layer 222 of the funnel, and FIG. 2M illustrates an embodiment of the expandable member 210 with a membrane 228 disposed between outer layer 222 and the inner layer 224 of the funnel. In some embodiments, the expandable member 210 may include a plurality of membranes 228 (e.g., a membrane 228 disposed upon the outer layer 222 of the funnel, and another membrane 228 disposed between outer layer 222 and the inner layer 224 of the funnel). In some embodiments, the membrane 228 covers at least half (e.g., 50% to 100%) of the outer layer 222 and/or the inner layer 224. In other embodiments, the membrane 228 substantially covers (e.g., covers 80% to 100%) of the outer layer 222 and/or the inner layer 224.

It noted that the membrane 228 is preferably between layers or outside the funnel formed by the expandable member 210 so that the agitator 218 does not come into contact with (and possibly damage) the membrane 228. In some embodiments, the agitator 218 is fully or mostly bounded by the inner layer 224 of the expandable member 210, which may be formed from nitinol, another metal, and/or another sufficiently durable material. Alternatively, the membrane 228 itself (if located on the inner surface of the funnel) may be formed from a sufficiently durable material so that it cannot be shredded by the agitator 218.

Any number of the presently disclosed elements may be suitable for imaging by a non-invasive imaging technology (e.g., X-ray, CT scans, etc.). For instance, the catheter 206, microcatheter 214, delivery tool 216, expandable member 210, agitator 218, guide stops 204, base member 212 and/or any additional components may comprise radiodense or radiopaque material (e.g., titanium, tungsten, barium sulfate, or zirconium oxide) suitable for insertion in a human body.

It is to be understood that any number of components of the obstruction removal system 200 may be attached by any suitable means including, but not limited to, welding, adhesive, mechanical fastening, interference fittings, etc. For example, the base member 212 may be attached to the expandable member 210 by such means. Alternatively, or additionally, two or more of the components may be portions of a common structure (e.g., a common mold, print, or mesh structure).

In some embodiments, the expandable member 210 is temporarily attached to the delivery tool 220. For example, the expandable member 210 may be configured to detach from the delivery tool 220 after base member 212 engages the one or more guide stops 204.

The base member 212 and guide stop(s) 204 may be configured to selectively engage and disengage. It is envisioned that the ability to selectively engage and disengage may provide advantages. For example, the ability to selectively disengage may allow for reusability of one or more of the components (e.g., expandable member 210, delivery tool 220, catheter 206, etc.). By way of another example, the ability to engage and disengage may provide increased functionality when inserting and removing components through the catheter 206 (e.g., fewer components translating through the catheter 206 at the same time).

It is envisioned that there may be multiple orders in which one or more devices of the obstruction removal system 200 are deployed. Factors for determining an order may include, but are not limited to, vasculature properties (e.g., vasculature size, vasculature geometries, branches of the vasculature, vasculature wall strength, etc.), blood pressure, blood flow direction, duration of operation (i.e., does patient require a reduced operating time for safety concerns), size of obstruction, or the configuration of the obstruction removal device.

Referring generally to FIGS. 2A through 2H, a method of removing an obstruction 208 from a vasculature 202 may include, but is not limited to, the steps of: inserting a catheter 206 within a vasculature 202, the catheter 206 having one or more guide stops 204 located at a distal end of the catheter 206 (FIG. 2A); inserting an expandable member 210 through the catheter 206 and at least partially extending the expandable member 210 into the vasculature 202 from the distal end of the catheter 206, the expandable member 210 including a base member 212 configured to engage the one or more guide stops 204 at the distal end of the catheter 206 (FIGS. 2B and 2C); transitioning the expandable member 210 from a contracted state to an expanded state after the expandable member 210 is at least partially extended into the vasculature 202 from the distal end of the catheter 206 (FIGS. 2C and 2D); inserting an agitator 218 through the catheter 206 and at least partially extending the agitator 218 from the distal end of the catheter 206 (FIGS. 2E and 2F); suctioning an obstruction 208 from the vasculature 202 into the catheter 206, wherein the expandable member 210 is configured to at least partially surround the obstruction 208 as the obstruction 208 is being suctioned into the catheter 206 to remove the obstruction 208 from the vasculature 202 (FIG. 2G); and breaking apart the obstruction 208 with the agitator 218 as the obstruction 208 is being suctioned through the expandable member 210 into catheter 206 to remove the obstruction 208 from the vasculature 202 (FIG. 2H).

In some implementations, the system 200 can be used in stages based on the situational requirements. For example, the catheter 206 may initially be used as a standalone catheter without the use of the expandable member 210 or the agitator 218. For example, a user may advance the catheter 206 up to the proximal end of the obstruction 208. Then, a suction device connected to the catheter 206 may be activated/actuated on to aspirate the obstruction 208. If aspiration fails, the expandable member 210 can be advanced through the catheter 206 up to the distal end of the catheter 206. If aspiration fails again, the agitator 218 may then be advanced through the catheter 206 up to and inside the funnel formed by the expandable member 210. The agitator 218 can be actuated back and forth and/or rotated within the funnel formed by the expandable member 210 to break up the obstruction 208 into small pieces 209 so that the obstruction 208 (i.e., the pieces 209) can be suctioned into the catheter 206.

Although the agitator 218 is described with reference to system 200 and expandable member 210, in other embodiments, the agitator 218 may be used in conjunction with other systems or devices described herein. For example, the obstruction removal device 109 in place of the expandable member 210 illustrated in FIGS. 2A through 2M, or alternatively, the agitator 218 can be used in conjunction with system 100.

Referring now to FIGS. 3A through 3L, an obstruction removal system is described, in accordance with one or more additional embodiments of this disclosure. In particular, FIGS. 3A through 3L illustrate embodiments of an obstruction removal system configured to selectively deploy an expandable member in a vasculature to reduce the risks associated with removal of an obstruction. The expandable member may be used to prevent an obstruction from dislodging from a stentriever and passing to a potentially more dangerous area (e.g., causing a total blockage, blocking a portion of a vital vasculature, etc.). In this regard, a physician may determine whether an obstruction is prone to risk and selectively deploy the expandable member. Furthermore, the physician may deploy the expandable member at various locations away from the obstruction (e.g., clot), as needed.

In embodiments, the obstruction removal system comprises a catheter (e.g., guide catheter, intermediate catheter, aspiration catheter, or the like), a delivery tool (e.g., guide wire or tube), an expandable member, and first and second locking members. The first locking member may be attached to the base of the expandable member, such that actuation of the expandable member results in actuation of the first locking member. The first locking member may be further configured to engage the second locking member. In this regard, the expandable member may be fixed to the second locking member by the first locking member.

The expandable member may be inserted within the catheter by a delivery tool and/or microcatheter and disposed proximate to an obstruction in the vasculature. The delivery tool and/or microcatheter may be further configured to engage the first locking member to the second locking member.

The expandable member may be configured to transition between one or more positions, such as, a contracted state and an expanded state. The expanded state may allow the expandable member to surround a portion of at least one of the stentriever and/or the obstruction. The contracted state may be suitable for insertion and removal of the expandable member through the catheter and/or a microcatheter. In this regard, when the expandable member is in the collapsed/contracted state after surrounding at least a portion of the stentriever and/or the obstruction, the expandable member, and the stentriever may be withdrawn through the catheter and/or the microcatheter.

Benefits for surrounding a portion of the stentriever or the obstruction in an expandable member may include, but are not limited to, smaller cross-sectional area, reduced friction on a vessel wall, reduced likelihood of catching on an opening of the catheter, reduced likelihood of catching on an opening of a microcatheter, and reduced likelihood of obstruction dislodgement.

The expandable member is configured to transition between the one or more positions (e.g., contracted state and collapsed position) in any suitable way, including, but not limited to, internal stresses, friction, material properties, wires attached to the expandable member, hooks to grab on to/make contact with a portion of a vessel wall, or a mating surface between the first locking member and the second locking member.

In some embodiments, the first locking member may be configured to disengage from the second locking member when the delivery system is removed from the vasculature. In this regard, the disengagement of the first locking member from the second locking member may be used to remove the stentriever and obstruction from the vasculature. The ability to disengage the first and second locking member may allow reuse of the delivery tool, the stentriever, the expandable member, the catheter, and/or the microcatheter. The first and second locking member may engage by any suitable means, including but not limited to, guide stops, snap-fit connectors, cooperatively threaded connectors, magnetic connectors, or the like.

In embodiments, the second locking member may be attached in several locations, including, but not limited to, the stentriever, the delivery tool, or an inner surface of the catheter. In this regard, after the first and second locking member engage, the first and second locking member will be fixed relative to the stentriever, the delivery tool, or the catheter.

It is to be understood that the first and second locking member may be configured to engage at various points during the removal of the obstruction from the vasculature. For example, the first and second locking member may engage before or after the stentriever engages the obstruction. The order of engagement listed is not intended to be limiting.

Figure 3A:
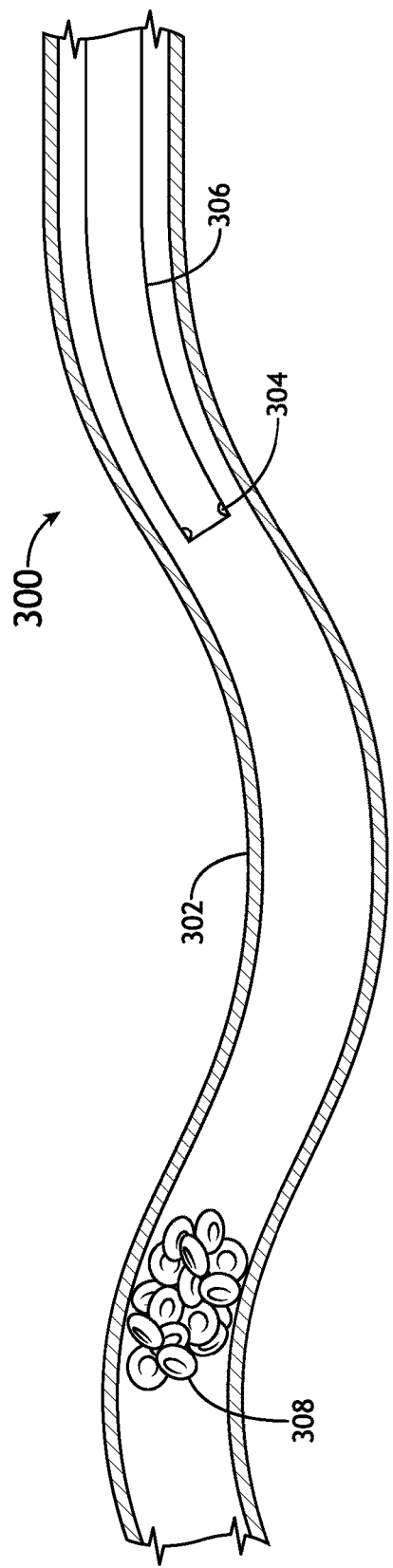
FIG. 3A illustrates a cross-sectional side view of a catheter of an obstruction removal system deployed within a vasculature, in accordance with one or more embodiments of the present disclosure.

FIGS. 3A through 3K illustrate one or more embodiments of an obstruction removal system 300. As shown in FIG. 3A, the obstruction removal system 300 includes a catheter 306 (e.g., guide catheter, intermediate catheter, aspiration catheter, or the like) configured to be inserted through a vasculature to a position proximate to an obstruction 308. The obstruction removal system 300 may include guide stops 304 attached (e.g., mounted) to or formed on an inner surface of the catheter 306, at or near a distal end of the catheter 306 (e.g., near an opening of the catheter).

Figure 3B:
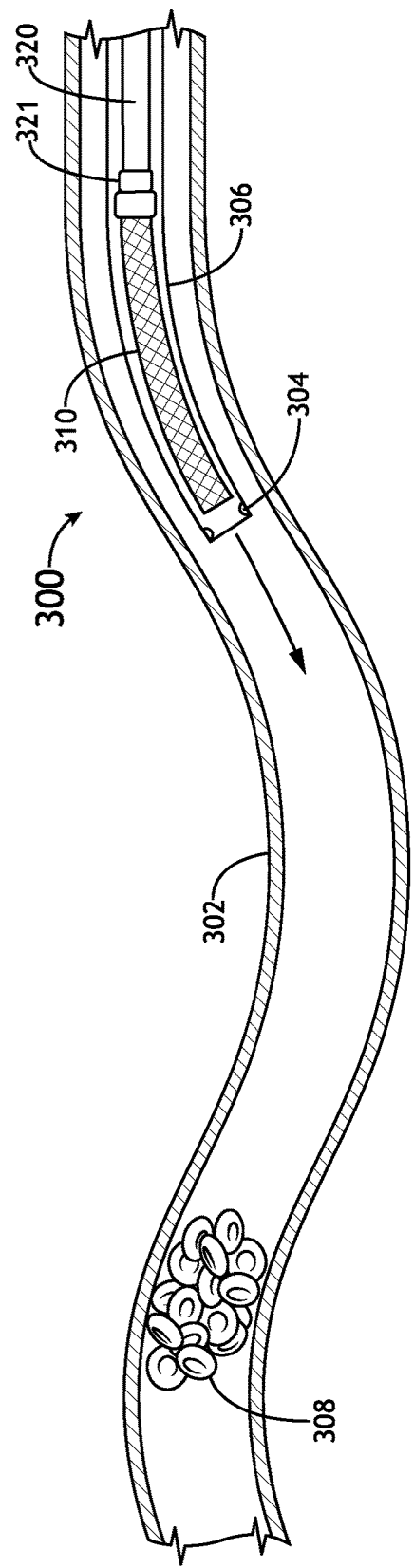
FIG. 3B illustrates a cross-sectional side view of an expandable member of the obstruction removal system being deployed through the catheter, in accordance with one or more embodiments of the present disclosure.

As shown in FIG. 3B, the obstruction removal system 300 further includes an expandable member 310. In a contracted state, the expandable member 310 is configured to be inserted through the catheter 306 and extended out of a distal opening of the catheter 306. When the expandable member 310 is in the contracted state, the expandable member may fit through the guide stops 304.

FIG. 3C illustrates the expandable member 310 deployed out of the distal opening of the catheter 306, where a base member 312 attached to the expandable member 310 is pushed up against, mated with, or otherwise engaged with the guide stops 304. A delivery tool 320 (e.g., a guide wire or tube) may be used to push the expandable member 310 through the catheter 306. In some embodiments, the delivery tool 320 may include an end-mounted support member 321 configured to support the expandable member 310 as the expandable member 310 is pushed through the catheter 306.

FIG. 3D illustrates the expandable member 310 transitioned to an expanded state. The delivery tool 320 can then be removed (e.g., withdrawn) from the catheter 306/vasculature 302. In the expanded state, the expandable member 310 may form a funnel with a first (proximal) opening that leads into the catheter 306 and a second (distal) opening that is configured to receive the obstruction 308 when the obstruction 308 is being removed from the vasculature 302. In this regard, the second (distal) opening is larger than the first (proximal) opening.

It is to be understood that the use of guide stops 304 on an inner portion of a catheter 306 may be suitable to allow a physician to selectively position the expandable member 310 at an appropriate distance from an obstruction 308 by translating some portion of the catheter 306 and/or the delivery tool 320. When positioning the catheter 306 and the expandable member 310, the physician may account for such things as vasculature geometry, obstruction size, blood pressure, blood flow direction, or vasculature tissue strength. For example, it may be undesirable to deploy the expandable member 310 near the obstruction location (e.g., due to a complex vasculature structure) but may still be desirable to use the expandable member 310 (e.g., to reduce likelihood of separation of the obstruction 308 from a stentriever). In this example, the expandable member 310 may be deployed away from the obstruction 308 and still retain the benefit of reducing complications due to obstruction dislodgement.

Figure 3E:
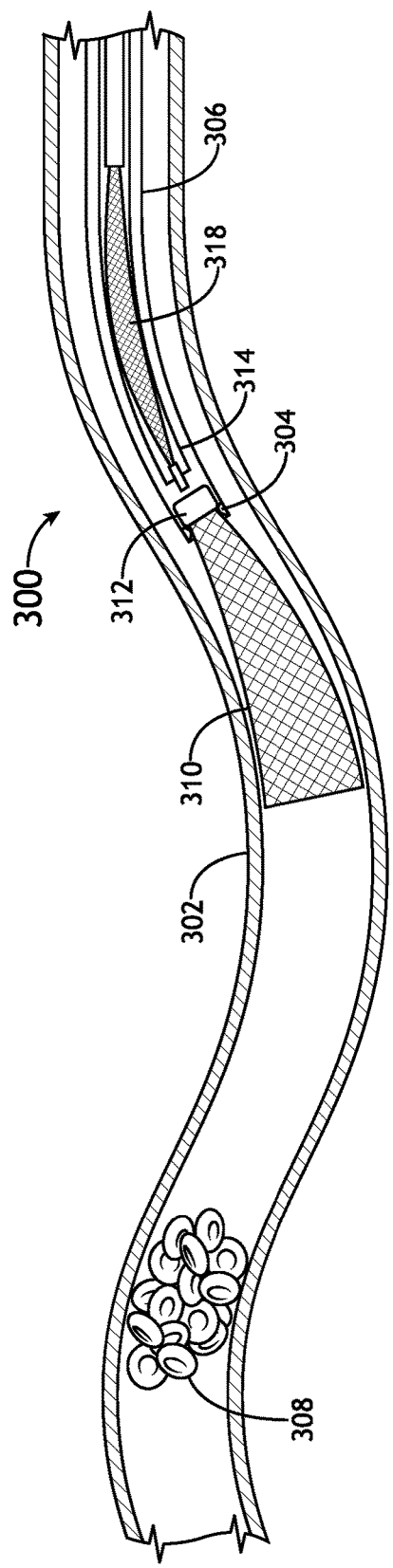
FIG. 3E illustrates a cross-sectional side view of a stentriever of the obstruction removal system being deployed through the catheter, wherein the stentriever is attached to a delivery tool that is fed through the catheter using a microcatheter, in accordance with one or more embodiments of the present disclosure.

Referring now to FIG. 3E, the obstruction removal system 300 may further include a stentriever 318 configured to be inserted through the catheter 306. For example, the stentriever 318 may be coupled or formed on/near a distal end of a delivery tool 316 (e.g., guide wire or tube) configured to be inserted through the catheter 306. In embodiments, the stentriever 318 may be housed within a microcatheter 314 (e.g., any suitable microcatheter or delivery tube). The microcatheter 314 may be used to contain the stentriever 318 and keep the stentriever 318 from expanding within the catheter 306. This may provide one or more advantages, such as, but not limited to, reducing friction between the stentriever 318 and the catheter 306, permitting the stentriever 318 to be inserted through the base member 312 and/or the distal opening of the catheter 306, and preventing the stentriever 318 from prematurely engaging with the expandable member 310.

Figure 3F:
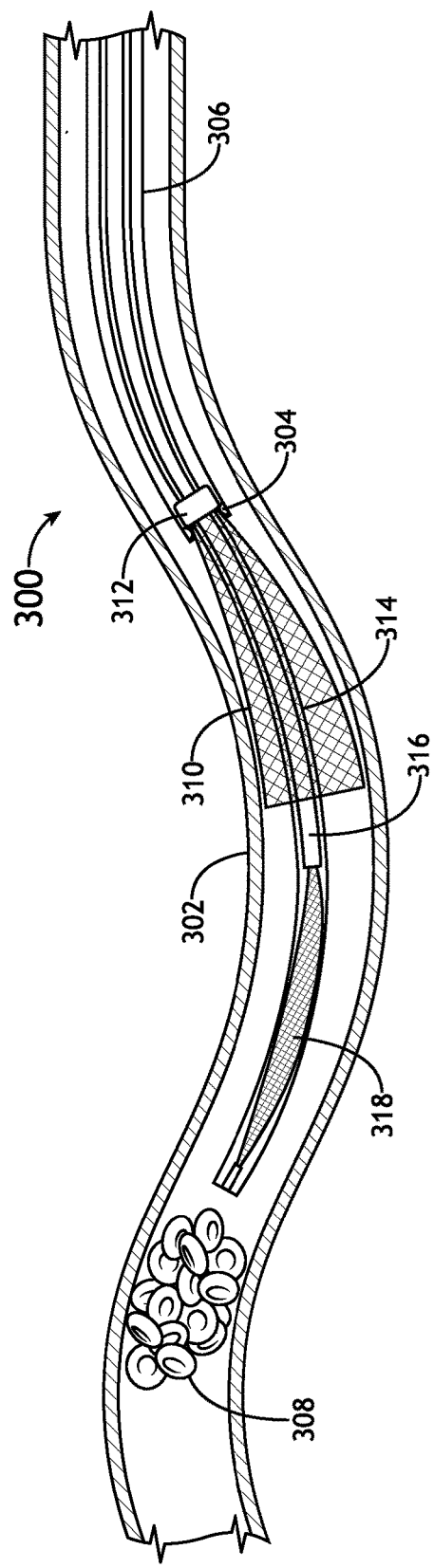
FIG. 3F illustrates a cross-sectional side view of the stentriever of the obstruction removal system being deployed through the catheter, wherein the stentriever attached to the delivery tool is fed through the catheter and the expandable member using the microcatheter, in accordance with one or more embodiments of the present disclosure.

FIG. 3F illustrates the stentriever 318, microcatheter 314, and delivery tool 316 inserted through the base member 312, the expandable member 310, and the distal opening of the catheter 306. The stentriever 318 is attached to the delivery tool 316, so that actuation of the delivery tool 316 results in actuation of the stentriever 318.

Figure 3G:
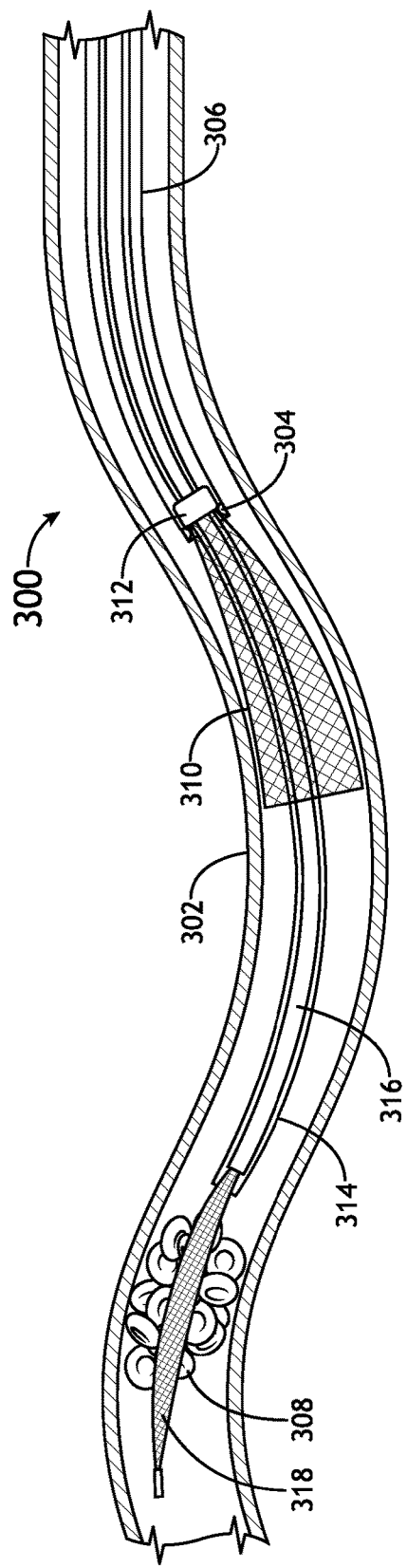
FIG. 3G illustrates a cross-sectional side view of the stentriever of the obstruction removal system being deployed within the vasculature, wherein the microcatheter is pulled back to unsheathe the stentriever so that the stentriever can engage an obstruction in the vasculature, in accordance with one or more embodiments of the present disclosure.

FIG. 3G illustrates the stentriever 318 after the stentriever 318 has been deployed out of a distal end of the microcatheter 314 and at least partially engaging the obstruction 308. It is to be understood that there may be one or more methods for engaging the obstruction 308 with the stentriever 318. For example, the microcatheter 314 may be deployed through/alongside of the obstruction 308, with the stentriever 318 contained within the microcatheter 314. The microcatheter 314 may then be withdrawn, permitting the stentriever 318 to expand and engage the obstruction 308.

Figure 3H:
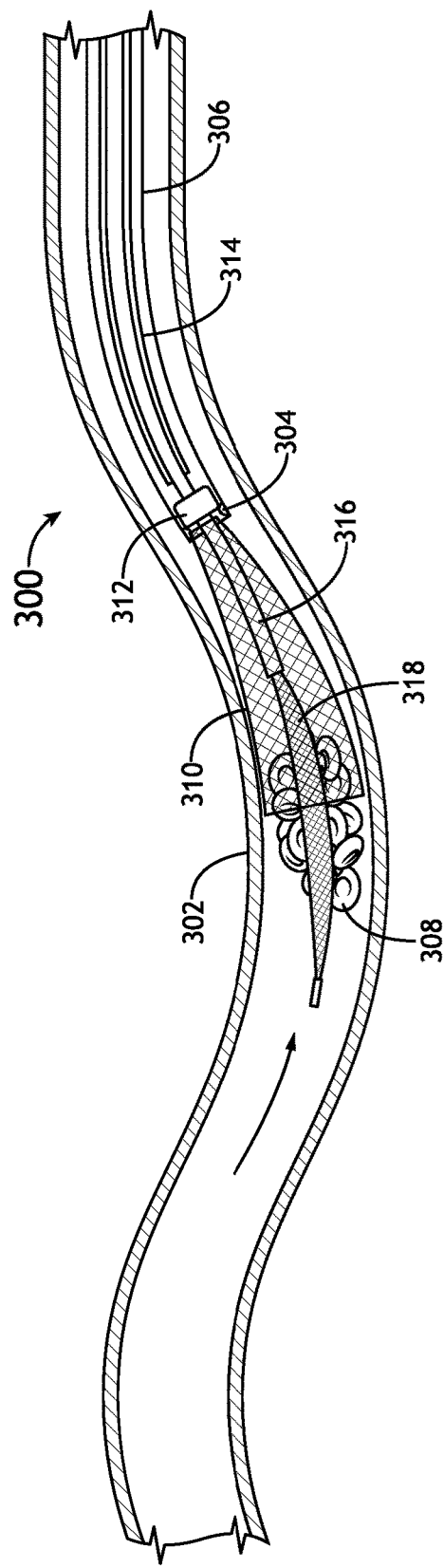
FIG. 3H illustrates a cross-sectional side view of the stentriever of the obstruction removal system being drawn into the catheter to remove the obstruction from the vasculature, in accordance with one or more embodiments of the present disclosure.

FIGS. 3H and 3I illustrate the delivery tool 316 withdrawing the stentriever 318 (and the obstruction 308) towards the expandable member 310. The expandable member 310 may be configured in an expanded state, such that the expandable member 310 may surround at least a portion of the obstruction 308 and/or stentriever 318 as the stentriever 318 and the obstruction 308 are pulled into the catheter 306. As the delivery tool 316 is withdrawn and removed from the vasculature, the expandable member 310 may transition from the expanded state to a contracted/collapsed state, thereby causing the expandable member 310 to at least partially surround and clench the obstruction 308 so that the obstruction 308 can be safely removed from the vasculature.

FIG. 3J illustrates the expandable member 310 withdrawn into the catheter 306 in a collapsed position. In some embodiments, the base member 312 may be configured to disengage from the guide stops 304. The delivery tool 316 with the stentriever 318, obstruction 308, and expandable member 310 may be withdrawn through the microcatheter 314, as depicted in FIG. 3J. Alternatively, the delivery tool 316 with the stentriever 318, obstruction 308, and expandable member 310 may be pulled directly through the catheter 306.

In some embodiments, the expandable member 310 has a wire (much like wire 113) coupled to the base member 312 and extended all the way through the catheter 306. This wire can prevent the expandable member 310 from being unintentionally ejected from the distal end of the catheter 306 should the base member 312 become disengaged from the guide stops 304. The wire can also be used to withdraw the expandable member 310 from the vasculature 302 (i.e., by pulling the wire to remove the expandable member 310 by pulling it through the catheter 306).

Figure 3K:
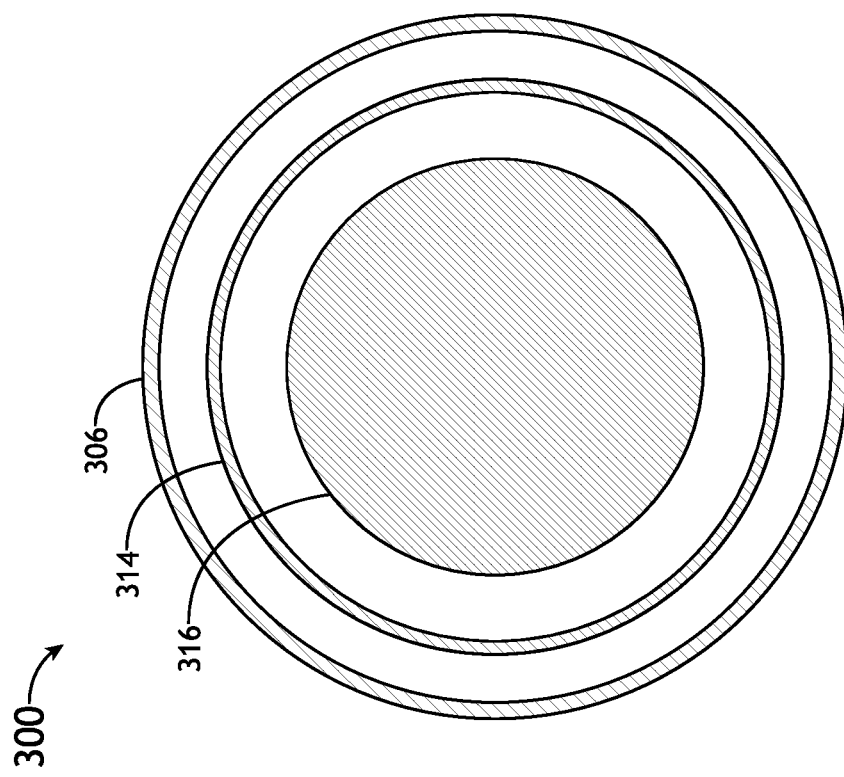
FIG. 3K illustrates a cross-sectional end view of a catheter with a microcatheter inserted within the catheter and a delivery tool inserted within the microcatheter, in accordance with one or more embodiments of the present disclosure.
Figure 3L:
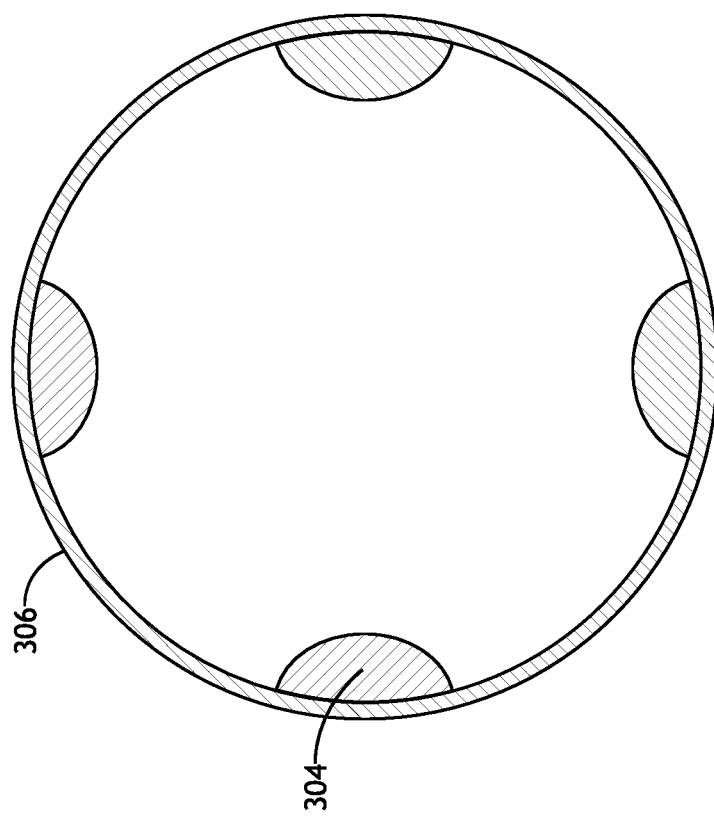
FIG. 3L illustrates a cross-sectional end view of a catheter with guide stops attached to an inner surface of the catheter, in accordance with one or more embodiments of the present disclosure.

FIG. 3K illustrates a cross-sectional end view of an obstruction removal system, where a delivery tool 316 is inserted through a microcatheter 314 and a catheter 306, and FIG. 3L illustrates a cross-sectional end view of a catheter 306 with guide stops 304 (e.g., one or more protrusions or a ring) attached to an inner surface of the catheter 306. The depicted guide stops 304 are non-limiting examples of means for engaging a base member. Additional structures or geometries may be used without deviating from the scope of this disclosure. The guide stops 304 may be configured to engage with a base member 312 attached to an expandable member 310 (e.g., by taking up a portion of the cross-sectional area of the catheter 306). Additionally, the guide stops 304 may be configured to take up a minimal cross-sectional area of the catheter 306, in order to allow injection of radioactive dye. In some embodiments, the guide stops 304 may be further configured to mate with the base member 312 to temporarily lock it in place at the distal end of the catheter 306.

Referring generally to embodiments of the obstruction removal system 300 disclosed herein, the expandable member 310 may be configured to transition between a first configuration and a second configuration, or between a contracted state and an expanded state, in any number of ways, including, but not limited to, unsheathing (e.g., withdrawal of the microcatheter 314 or extension through the catheter 306), disengagement of locking members (e.g., wires, hooks, etc.) attached to the expandable member 310, use of shape memory alloys (e.g., Nitinol), or the like. It is envisioned that when the expandable member is in an expanded state, the expandable member may take up a substantial portion (e.g., 80% or more) of the cross-section of the vasculature 302.

In embodiments, the expandable member 310, the obstruction 308, and the stentriever 318 are withdrawn into the catheter 306 and removed from the vasculature. In some embodiments, the expandable member 310, the obstruction 308, and the stentriever 318 may be further withdrawn into the microcatheter 314. The expandable member 310 may surround at least a portion of the obstruction 308 to prevent dislodging and may also assist in compressing the obstruction 308 into the catheter 306 and/or the microcatheter 314 (e.g., by tension, cinching, crimping, etc.).

In some embodiments, an expandable member 310 may further include one or more features including, but not limited to, hooks. The hooks may attach to or make abrasive contact with a vessel wall when the expandable member 310 is in the expanded state; the hooks may also hold a portion of the obstruction 308 when the expandable member 310 at least partially surrounds the obstruction 308 prior to its removal.

Surrounding at least a portion of the obstruction 308 and/or stentriever 318 by the expandable member 310 may serve several functions including, but not limited to, reducing a likelihood that the stentriever 318 snags (e.g., on a vessel wall of the vasculature 302 or an opening of the catheter 306), reducing a profile of the obstruction 308 for removal through the catheter 306 and/or microcatheter 314, and/or securing the obstruction 308 to prevent dislodgement from the stentriever 318.

In embodiments, the expandable member 310 may comprise a wire mesh. Such a wire mesh may include wires made of a flexible material (e.g., nitinol, cobalt chromium, polymer mesh, or the like), where the wires (e.g., 16 to 288 or more wires), have a certain diameter (e.g., from 0.0007 inches to 0.0050 inches), and have certain material properties (e.g., strength, coefficient of friction with blood, resistance to plastic deformation, etc.) suitable for engaging the obstruction 308 and/or the stentriever 318. Furthermore, the wire mesh may include various sets of wires (e.g., support wires with larger diameters, wires to engage a vessel wall, wires to engage a portion of the obstruction or stentriever, radiopaque or radiodense wires, etc.).

Any number of the presently disclosed elements may be suitable for imaging by a non-invasive imaging technology (e.g., X-ray, CT scans, etc.). For instance, the catheter 306, delivery tool 316, microcatheter 314, expandable member 310, stentriever 318, guide stops 304, base member 312 and/or any additional components may comprise radiodense or radiopaque material (e.g., titanium, tungsten, barium sulfate, or zirconium oxide) suitable for insertion in a human body.

It is to be understood that any number of components of the obstruction removal system 300 may be attached by any suitable means including, but not limited to, welding, adhesive, mechanical fastening, interference fittings, etc. For example, the base member 312 may be attached to the expandable member 310 by such means. Alternatively, or additionally, two or more of the components may be portions of a common structure (e.g., a common mold or print).

In some embodiments, the expandable member 310 is temporarily attached to the microcatheter 314. For example, the expandable member 310 may be configured to detach from the microcatheter 314 after base member 312 engages the one or more guide stops 304.

The base member 312 and guide stop(s) 304 may be configured to selectively engage and disengage. It is envisioned that the ability to selectively engage and disengage may provide advantages. For example, the ability to selectively disengage may allow for reusability of one or more of the components (e.g., expandable member 310, microcatheter 314, catheter 306, etc.). By way of another example, the ability to engage and disengage may provide increased functionality when inserting and removing components through the catheter 306 (e.g., fewer components translating through the catheter 306 at the same time).

It is envisioned that there may be multiple orders in which one or more devices of the obstruction removal system 300 are deployed. Factors for determining an order may include, but are not limited to, vasculature properties (e.g., vasculature size, vasculature geometries, branches of the vasculature, vasculature wall strength, etc.), blood pressure, blood flow direction, duration of operation (i.e., does patient require a reduced operating time for safety concerns), size of obstruction, or the configuration of the obstruction removal device.

Referring generally to FIGS. 3A through 3J, a method of removing an obstruction from a vasculature may include, but is not limited to, the steps of: deploying the catheter 306 through the patient's vasculature to a position near the obstruction 308, where the catheter 306 includes one or more guide stops 304 on an inner surface at the distal end of the catheter 306; inserting the expandable member 310 through the catheter 306 and (with a delivery tool 320) pushing the expandable member 310 up to the distal end of the catheter 306, so that a base member 312 attached to the expandable member 310 engages the guide stops 304; inserting the stentriever 318 attached to delivery tool 316 within a microcatheter 314 and feeding the stentriever 318 through the catheter 306 using the microcatheter 314; deploying the stentriever 318 and the microcatheter 314 through the catheter 306, guide stops 304, and expandable member 310 up to the obstruction 308; withdrawing the microcatheter 314 to unsheathe the stentriever 318 in order to engage the obstruction 308 with the stentriever 318; withdrawing the stentriever 318 and the obstruction 308 by withdrawing (e.g., pulling) the delivery tool 316, where the expandable member 310 surrounds at least a portion of the obstruction 308 and/or the stentriever 318 and transitions from an expanded state to a contracted state as the delivery tool 316 with the stentriever 318 and obstruction 308 are pulled through the catheter 306 and removed from the vasculature.

Referring now to FIGS. 4A through 4F, an obstruction removal system is described, in accordance with one or more additional embodiments of this disclosure. In particular, FIGS. 4A through 4F illustrate embodiments of an obstruction removal system configured to deploy an expandable member within a vasculature to reduce the risks associated with removal of an obstruction when the obstruction is suctioned into and/or pulled through a catheter to remove the obstruction from the vasculature. The expandable member may be used to prevent an obstruction from passing to a potentially more dangerous area (e.g., causing a total blockage, blocking a portion of a vital vasculature, etc.). In this regard, a physician may determine whether an obstruction is prone to risk and selectively deploy the expandable member. Furthermore, the physician may deploy the expandable member at various locations away from the obstruction (e.g., clot), as needed.

In embodiments, the obstruction removal system includes a catheter configured to be inserted within a vasculature. The catheter includes an expandable member surrounding a portion of the catheter that is near a distal end of the catheter. The expandable member may be introduced into the vasculature when the catheter (e.g., an aspiration catheter) is extended into the vasculature to engage and remove an obstruction (e.g., using suction force). The expandable member may be configured to invert from a first orientation to a second orientation in order to cover the distal end of the catheter and the obstruction engaged by the distal end of the catheter. This action may occur before or while the catheter is being pulled back out of the vasculature to remove the obstruction, which is held to the catheter by suction force, from the vasculature. In this manner, the expandable member is further configured to at least partially surround the obstruction as the obstruction is being removed from the vasculature. The expandable member helps prevent the obstruction (or portions thereof) from being dislodged into the vasculature.

Figure 4A:
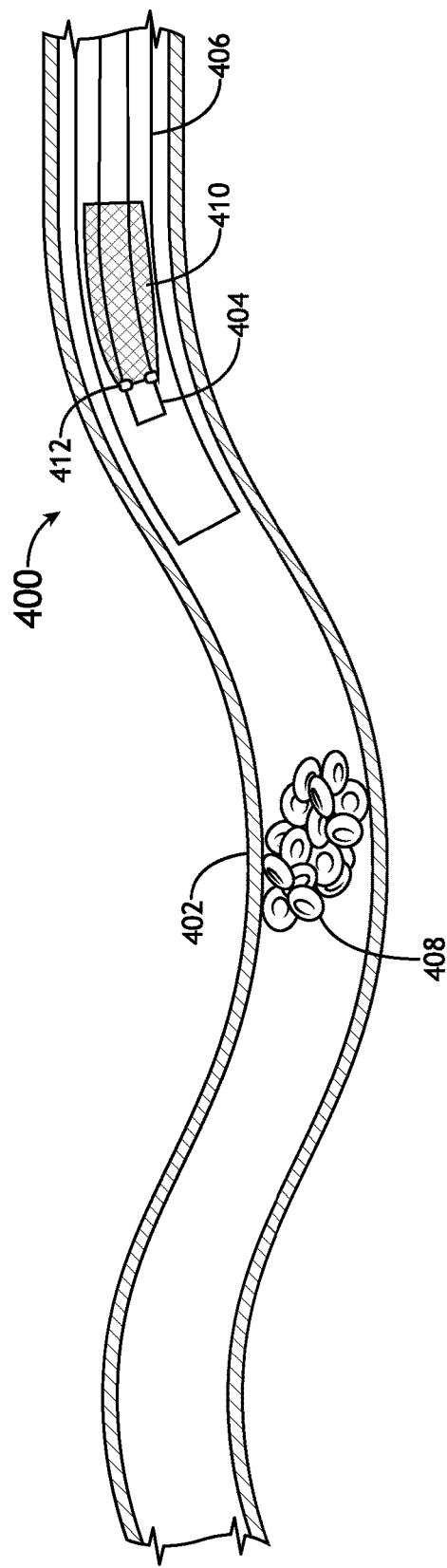
FIG. 4A illustrates a cross-sectional side view of an aspiration catheter and a guide catheter of an obstruction removal system deployed within a vasculature, wherein the aspiration catheter includes an expandable member surrounding a portion of the aspiration catheter near a distal end of the aspiration catheter, in accordance with one or more embodiments of the present disclosure.
Figure 4B:
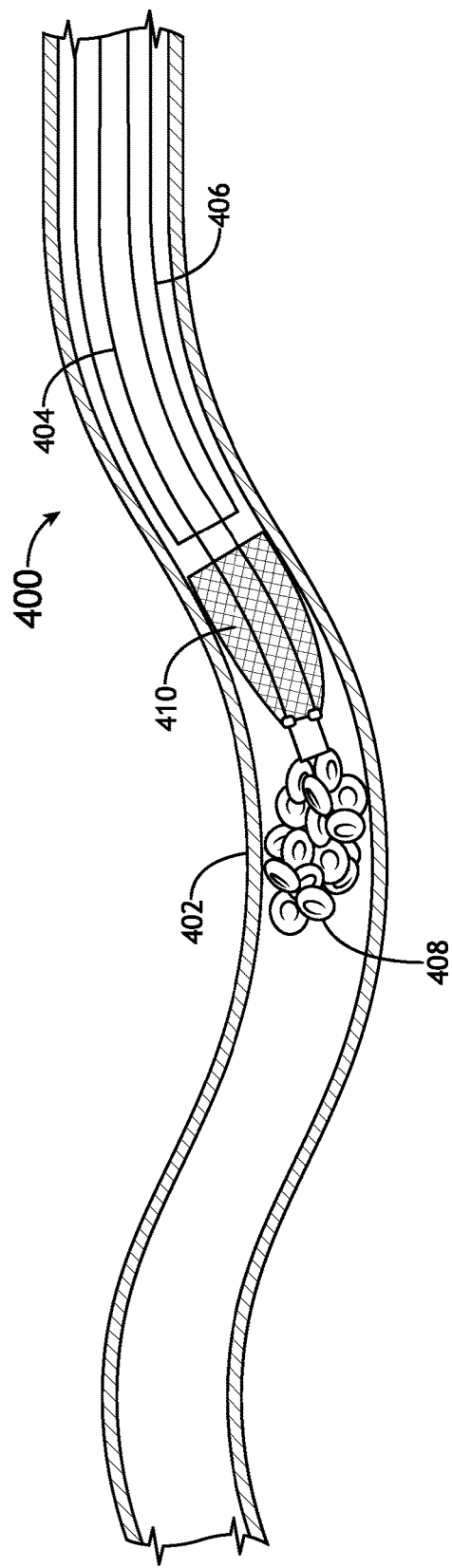
FIG. 4B illustrates a cross-sectional side view the aspiration catheter being deployed through the guide catheter to engage an obstruction within the vasculature, in accordance with one or more embodiments of the present disclosure.

FIGS. 4A through 4F illustrate one or more embodiments of an obstruction removal system 400. As shown in FIGS. 4A and 4B, the obstruction removal system 400 includes a catheter 404 (e.g., an aspiration catheter, intermediate catheter, or the like) configured to be inserted through a vasculature 402 to a position proximate to an obstruction 408. The obstruction removal system 400 may further include a guide catheter 406 configured to be inserted through the vasculature 402 before catheter 404 so that catheter 404 can be fed through the guide catheter 406.

In embodiments, the catheter 404 is configured to remove the obstruction 408 from the vasculature 402 when a suction force is applied to the catheter 404. For example, the catheter 404 may be coupled to a pump, syringe, vacuum chamber, or any other suction device configured to selectively produce negative pressure in the catheter 404 so that the obstruction 408 is drawn into (and/or suctioned onto) the catheter 404 to remove the obstruction 408 from the vasculature 402.

Figure 4C:
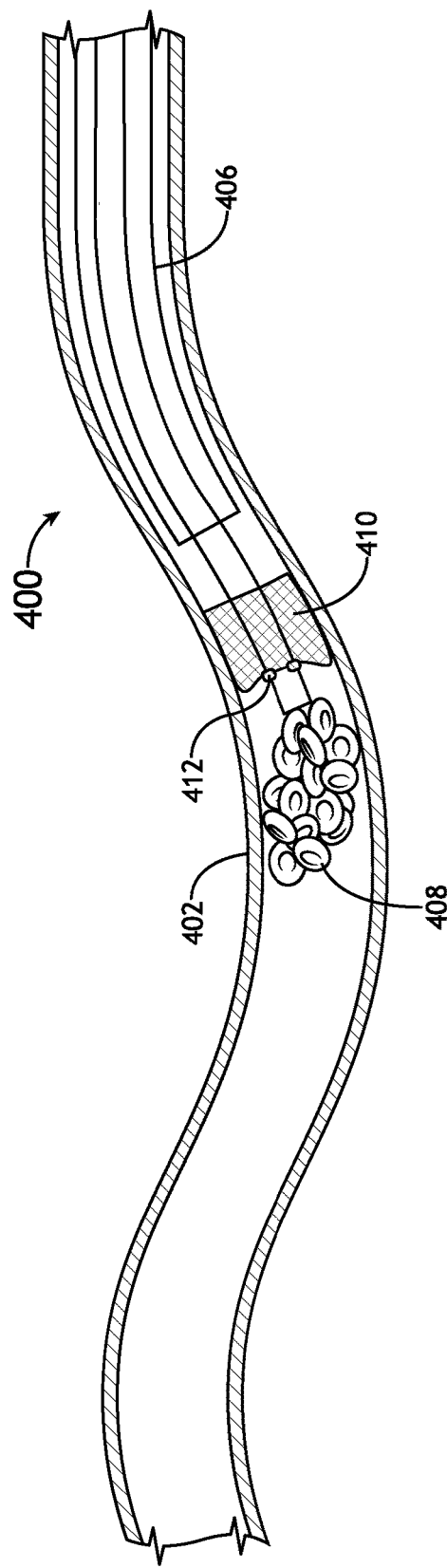
FIG. 4C illustrates a cross-sectional side view the expandable member inverting as the aspiration catheter applies a suction force to the obstruction within the vasculature, in accordance with one or more embodiments of the present disclosure.
Figure 4D:
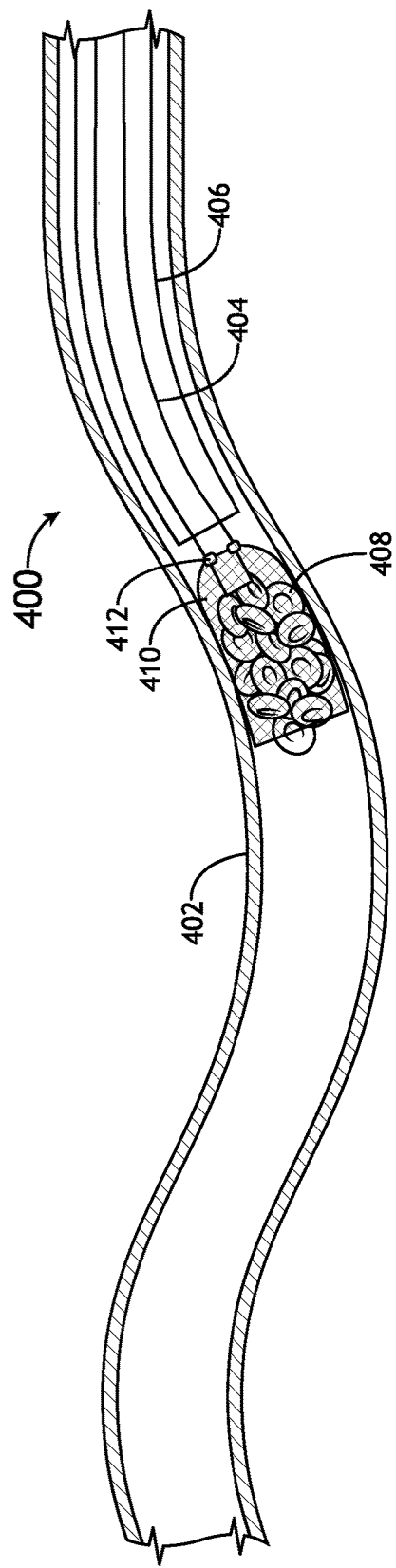
FIG. 4D illustrates a cross-sectional side view the expandable member inverted over the distal end of the aspiration catheter and at least a portion of the obstruction, which is held to the distal end of the aspiration catheter by the suction force, in accordance with one or more embodiments of the present disclosure.

The obstruction removal system 400 further includes an expandable member 410 that is coupled to the catheter 404. In embodiments, the expandable member 410 is a tubular or funnel shaped mesh with one free end and one fixed end that is affixed to the catheter 404 (e.g., by one or more fasteners 412, such as a marker band, glue, molding, welding, etc.) in such a way that the expandable member 410 surrounds a portion of the catheter 404 that is near a distal end of the catheter 404. In a first orientation, the expandable member 410 trails behind the distal end of the catheter 404. For example, the expandable member 410 is configured to trail behind the distal end of the catheter 404 while the catheter is being inserted through the guide catheter 406 and/or vasculature 402. As shown in FIGS. 4C and 4D, the expandable member 410 is configured to be selectively inverted to a second orientation so the expandable member 410 covers the distal end of the catheter 404 and surrounds at least a portion of the obstruction 408. For example, the expandable member 410 may be inverted as a result of friction between the expandable member 410 and the vasculature 402 or the fluid flowing therethrough when the catheter 404 is pulled back through the guide catheter 406 and/or vasculature 402 in order to remove the catheter 404 and the obstruction 408, which is being suctioned by the catheter 404, from the vasculature 402.

FIGS. 4C and 4D illustrate the expandable member 410 transitioning (i.e., inverting) from a first orientation to a second orientation. In the second orientation (sometimes referred to as the "inverted state"), the expandable member 410 may form a basket or funnel with a first (proximal) opening that surrounds a portion of the catheter 404 and a second (distal) opening that is configured to surround the obstruction 408 while the obstruction 408 is being suctioned into the catheter 404 to remove the obstruction 408 from the vasculature 402. In this regard, the second (distal) opening is larger than the first (proximal) opening.

It is to be understood that the use of a guide catheter 406 may allow a physician to selectively position catheter 404 relative to the obstruction 408 by translating catheter 404 relative to the guide catheter 406. When positioning the catheter 404 and the expandable member 410, the physician may account for such things as vasculature geometry, obstruction size, blood pressure, blood flow direction, or vasculature tissue strength. For example, in some instances, it may be undesirable to deploy the expandable member 410 near the obstruction location (e.g., due to a complex vasculature structure) but may still be desirable to use the expandable member 410 (e.g., to reduce/control debris separated from the obstruction 408 when the obstruction is being removed from the vasculature 402). In this regard, the expandable member 410 may be deployed away from the obstruction 408 and still retain the benefit of reducing complications that may be caused by dislodgement or breaking up of the obstruction 408.

In use, the obstruction removal system 400 is configured to apply a suction force from the catheter 404 to an obstruction 408 to remove the obstruction 408 from the vasculature 402. The expandable member 410 surrounds a distal portion of the catheter 404 and is configured to transition from a first (trailing) orientation to an inverted state after the expandable member 410 is at least partially extended into the vasculature 402 and then pulled back (e.g., to withdraw the catheter 404). The change in direction when the expandable member 410 is pulled back subjects the expandable member 410 to frictional forces (or resistive forces) resulting from contact with inner surfaces of the vasculature 402 or resistance from the fluid flowing therethrough. After inverting, the expandable member 410 is configured to at least partially surround the obstruction 408 as the obstruction 408 is being removed from the vasculature 402. In this manner, the expandable 410 member helps prevent the obstruction 408 (or portions thereof) from being dislodged into the vasculature 402.

The catheter 404 can be placed into contact with (or in close proximity of) the obstruction 408 so that the obstruction 408 can be suctioned into the catheter 414. In some cases, the obstruction 408 (or a portion thereof) may be too hard to suction into the catheter 404; as a result, the obstruction 408 may become stuck onto the distal end of the catheter 404 (e.g., as shown in FIG. 4B). When this occurs, the catheter 404 carrying the obstruction 408 at its distal end can be pulled out of the vasculature 402 through the guide catheter 406 to remove the obstruction 408 from the vasculature 402. As shown in FIGS. 4C through 4F, the suction force holds the obstruction 408 to the distal end of the catheter 404 while the expandable member 410 inverts and surrounds the obstruction 408 so that the obstruction 408 can be safely pulled through the guide catheter 406 without dislodging or releasing any debris into the vasculature 402.

In some embodiments, the catheter 404 has a narrow diameter so that obstructions 408 are usually held at the distal end of the catheter 404 rather than being sucked up through the catheter 404 as they would typically be when using an aspiration catheter. This allows an obstruction 408 to be surrounded by the expandable member 410 and removed by withdrawing the catheter 404 with the obstruction 408 through the guide catheter 406, thereby preventing potential dislodging or release of debris that could occur when the obstruction 408 is suctioned out of the vasculature 402 using a typical aspiration catheter.

Nevertheless, when the obstruction 408 is soft enough, the suction force will cause portions of the obstruction 408 to break off or deform so that the obstruction 408 (or a portion thereof) is suctioned out of the vasculature 402 through the catheter 404. In some cases, the obstruction 408 can be fully aspirated. In other cases, part of the obstruction 408 may be aspirated and the remainder of the obstruction 408 may be removed by pulling the catheter 404 carrying the obstruction 408, surrounded by the expandable member 410, at its distal end through the guide catheter 406 to remove the obstruction 408 from the vasculature 402.

In some embodiments, the expandable member 410 may have a wire coupled to the expandable member 410 and extended all the way through the guide catheter 406. This wire can prevent the expandable member 410 from being unintentionally decoupled from the catheter 404. The wire can also be used to withdraw the expandable member 410 from the vasculature 402 (i.e., by pulling the wire to remove the expandable member 410 by pulling it through guide catheter 406).

Referring generally to embodiments of the obstruction removal system 400 disclosed herein, the expandable member 410 may be configured to transition between a first configuration (e.g., trailing orientation) and a second configuration (e.g., inverted orientation), or between a contracted state and an expanded state, in any number of ways, including, but not limited to, frictional or resistive forces resulting from contact with inner surfaces of the vasculature 402 or fluid flowing therethrough, unsheathing (e.g., extension through the guide catheter 406), disengagement of locking members (e.g., wires, hooks, etc.) attached to the expandable member 410, use of shape memory alloys (e.g., Nitinol), or the like. It is envisioned that when the expandable member is in an expanded/inverted state, the expandable member may take up a substantial portion (e.g., 80% or more) of the cross-section of the vasculature 402.

In embodiments, the expandable member 410 may comprise a wire mesh. Such a wire mesh may include wires made of a flexible material (e.g., nitinol, cobalt chromium, polymer mesh, or the like), where the wires (e.g., 16 to 288 or more wires), have a certain diameter (e.g., from 0.0007 inches to 0.0050 inches), and have certain material properties (e.g., strength, coefficient of friction with blood, resistance to plastic deformation, etc.) suitable for engaging the obstruction 408. Furthermore, the wire mesh may include various sets of wires (e.g., support wires with larger diameters, wires to engage a vessel wall, wires to engage a portion of the obstruction or stentriever, radiopaque or radiodense wires, etc.).

Any number of the presently disclosed elements may be suitable for imaging by a non-invasive imaging technology (e.g., X-ray, CT scans, etc.). For instance, the expandable member 410 (or any portion thereof), guide catheter 406, catheter 404, and/or any additional components of the obstruction removal system 400 may comprise radiodense or radiopaque material (e.g., titanium, tungsten, barium sulfate, or zirconium oxide) suitable for insertion in a human body.

It is to be understood that any number of components of the obstruction removal system 400 may be attached by any suitable means including, but not limited to, welding, adhesive, mechanical fastening, interference fittings, etc. For example, the catheter 404 may be attached to the expandable member 410 by such means. Alternatively, or additionally, two or more of the components may be portions of a common structure (e.g., a common mold, print, or mesh structure).

It is envisioned that there may be multiple orders in which one or more devices of the obstruction removal system 400 are deployed. Factors for determining an order may include, but are not limited to, vasculature properties (e.g., vasculature size, vasculature geometries, branches of the vasculature, vasculature wall strength, etc.), blood pressure, blood flow direction, duration of operation (i.e., does patient require a reduced operating time for safety concerns), size of obstruction, or the configuration of the obstruction removal device.

Referring generally to FIGS. 4A through 4F, a method of removing an obstruction 408 from a vasculature 402 may include, but is not limited to, the steps of: inserting a catheter 404 within a vasculature 402 (directly or by introducing the catheter 404 through a guide catheter 406), the catheter 404 having an expandable member surrounding a portion of the catheter 404 at or near a distal end of the catheter 404 (FIG. 4A); engaging the obstruction 408 in the vasculature 402 with the distal end of the catheter 404 and suctioning the obstruction 408 into/onto the distal end of the catheter 404 (FIG. 4B); inverting the expandable member 410 to cover or surround the distal end of the catheter 404 and at least a portion of the obstruction 408 with the inverted expandable member 410 (FIGS. 4C and 4D); and withdrawing the catheter 404 from the vasculature 402 (directly or through a guide catheter 406) to remove the obstruction 408, which is held onto the distal end of the catheter 404 by suction force and at least partially surrounded by the expandable member 410 (FIGS. 4E and 4F).

It is to be understood that implementations of the methods disclosed herein may include one or more of the steps described herein. Further, such steps may be carried out in any desired order and, in some implementations, two or more of the steps may be carried out simultaneously with one another. Two or more of the steps disclosed herein may be combined in a single step, and in some implementations, one or more of the steps may be carried out as two or more sub-steps. Further, other steps or sub-steps may be carried in addition to, or as substitutes to one or more of the steps disclosed herein.

It is also to be understood that usage of terminology in the present disclosure is not intended to be limiting. For example, as used herein, an "obstruction" may refer to any vascular obstruction, including but not limited to, a blood clot, plaque (e.g., fat, cholesterol, etc.), internal structure/growth, foreign object, or the like.

Although the technology has been described with reference to the embodiments illustrated in the attached drawing figures, equivalents may be employed, and substitutions may be made without departing from the scope of the technology as recited in the claims. Components illustrated and described herein are examples of a device and components that may be used to implement the embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. An obstruction removal system, comprising: an aspiration catheter configured to be inserted into a vasculature; and an obstruction removal device configured to be inserted through the aspiration catheter and at least partially extended into the vasculature from a distal end of the aspiration catheter, the obstruction removal device including: a tubular member configured to apply a suction force from the aspiration catheter to an obstruction to remove the obstruction from the vasculature; and an expandable member surrounding the tubular member, the expandable member being configured to transition from a contracted state to an expanded state after the expandable member is at least partially extended into the vasculature from the distal end of the aspiration catheter, the expandable member being further configured to at least partially surround the obstruction as the obstruction is being removed from the vasculature, wherein the expandable member comprises a wire mesh folded at a distal edge to form an outer layer and an inner layer that are bound together at a base member, and wherein a membrane is disposed between the outer layer and the inner layer to prevent or reduce fluid flow through the wire mesh, and wherein a proximal portion of the expandable member is configured to fold over the distal end of the aspiration catheter in order to prevent the expandable member from being suctioned into the aspiration catheter.

2. The obstruction removal system of claim 1, wherein a distal portion of the expandable member is configured to form a basket around the tubular member to at least partially surround the obstruction as the obstruction is being removed from the vasculature.

3. The obstruction removal system of claim 1, wherein the tubular member comprises a flexible polymer tube.

4. The obstruction removal system of claim 3, wherein the tubular member is structurally reinforced by a coil or a wire mesh.

5. The obstruction removal system of claim 1, further comprising:
a guide catheter, wherein the aspiration catheter is configured to be inserted into the vasculature through the guide catheter.

6. The obstruction removal system of claim 5, wherein the aspiration catheter and the obstruction removal device, carrying at least a portion of the obstruction surrounded by the expandable member, are configured to be withdrawn from the vasculature through the guide catheter when the obstruction cannot be fully suctioned into the aspiration catheter through the tubular member.

7. An obstruction removal device configured to be inserted through an aspiration catheter and at least partially extended into a vasculature from a distal end of the aspiration catheter, the obstruction removal device comprising: a tubular member configured to apply a suction force from the aspiration catheter to an obstruction to remove the obstruction from the vasculature; and an expandable member surrounding the tubular member, the expandable member being configured to transition from a contracted state to an expanded state after the expandable member is at least partially extended into the vasculature from the distal end of the aspiration catheter, the expandable member being further configured to at least partially surround the obstruction as the obstruction is being removed from the vasculature, wherein the expandable member comprises a wire mesh folded at a distal edge to form an outer layer and an inner layer that are bound together at a base member, and wherein a membrane is disposed between the outer layer and the inner layer to prevent or reduce fluid flow through the wire mesh, and wherein a proximal portion of the expandable member is configured to fold over the distal end of the aspiration catheter in order to prevent the expandable member from being suctioned into the aspiration catheter.

8. The obstruction removal device of claim 7, wherein a distal portion of the expandable member is configured to form a basket around the tubular member to at least partially surround the obstruction as the obstruction is being removed from the vasculature.

9. The obstruction removal device of claim 7, wherein the tubular member comprises a flexible polymer tube.

10. The obstruction removal device of claim 9, wherein the tubular member is structurally reinforced by a coil or a wire mesh.

11. The obstruction removal device of claim 7, wherein the obstruction removal device, carrying at least a portion of the obstruction surrounded by the expandable member, is configured to be withdrawn from the vasculature with the aspiration catheter through a guide catheter when the obstruction cannot be fully suctioned into the aspiration catheter through the tubular member.

* * * * *